(12) United States Patent
Benz et al.

(10) Patent No.: US 7,101,956 B2
(45) Date of Patent: Sep. 5, 2006

(54) COMPOUNDS CONTAINING QUATERNARY CARBONS, MEDICAL DEVICES, AND METHODS

(75) Inventors: Michael Eric Benz, Ramsey, MN (US); Edward DiDomenico, Anoka, MN (US); Christopher M. Hobot, Tonka Bay, MN (US); Randall V. Sparer, Andover, MN (US); Kenneth B. Wagener, Gainesville, FL (US); John E. Schwendeman, Pittsburgh, PA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 10/292,993

(22) Filed: Nov. 13, 2002

(65) Prior Publication Data

US 2003/0125499 A1 Jul. 3, 2003

Related U.S. Application Data

(60) Provisional application No. 60/332,695, filed on Nov. 14, 2001, and provisional application No. 60/361,254, filed on Mar. 1, 2002.

(51) Int. Cl.
*C08G 18/63* (2006.01)

(52) U.S. Cl. .................. 528/85; 525/123; 525/131

(58) Field of Classification Search ............... 525/123, 525/131; 528/85
See application file for complete search history.

(56) References Cited

U.S. PATENT DOCUMENTS

| | | | | |
|---|---|---|---|---|
| 3,948,829 A | * | 4/1976 | Babayan | ............. 524/313 |
| 4,208,506 A | | 6/1980 | Deichert et al. | |
| 4,276,394 A | | 6/1981 | Kennedy et al. | |
| 4,316,973 A | | 2/1982 | Kennedy et al. | |
| 4,568,732 A | | 2/1986 | Kennedy et al. | |
| 4,647,643 A | * | 3/1987 | Zdrahala et al. | |
| 4,746,715 A | | 5/1988 | Dworczak et al. | |
| 4,873,308 A | | 10/1989 | Coury et al. | |
| 4,883,854 A | | 11/1989 | Coury et al. | |
| 4,946,899 A | | 8/1990 | Kennedy et al. | |
| 5,040,544 A | | 8/1991 | Lessar et al. | ............. 128/784 |
| 5,073,381 A | | 12/1991 | Ivan et al. | |
| 5,110,885 A | | 5/1992 | Wagener et al. | |
| 5,147,725 A | | 9/1992 | Pinchuk | |
| 5,238,006 A | | 8/1993 | Markowitz | ............. 607/143 |
| 5,290,895 A | | 3/1994 | Wagener et al. | |
| 5,340,881 A | | 8/1994 | Kennedy et al. | |
| 5,375,609 A | | 12/1994 | Molacek et al. | |
| 5,476,509 A | | 12/1995 | Keogh et al. | |
| 5,480,421 A | | 1/1996 | Otten | ............. 697/122 |
| 5,561,210 A | * | 10/1996 | Roy | |
| 5,663,245 A | | 9/1997 | Kennedy et al. | |
| 5,736,251 A | | 4/1998 | Pinchuk | |
| 5,741,331 A | | 4/1998 | Pinchuk | |
| 5,986,034 A | | 11/1999 | DiDomenico et al. | ............. 528/72 |

| | | | | |
|---|---|---|---|---|
| 6,102,939 A | | 8/2000 | Pinchuk | |
| 6,111,052 A | | 8/2000 | DiDomenico et al. | ............. 528/72 |
| 6,149,678 A | | 11/2000 | DiDomenico et al. | ............. 607/122 |
| 6,197,240 B1 | | 3/2001 | Pinchuk | |
| 6,252,101 B1 | * | 6/2001 | Herzig et al. | |
| 6,313,254 B1 | * | 11/2001 | Meijs et al. | |
| 6,388,010 B1 | * | 5/2002 | St. Clair | ............. 525/130 |
| 6,420,452 B1 | * | 7/2002 | Gunatillake et al. | |
| 6,437,073 B1 | | 8/2002 | Gunatillake et al. | |
| 2002/0028901 A1 | | 3/2002 | Gunatillake et al. | |
| 2004/0054080 A1 | | 3/2004 | Benz et al. | |
| 2004/0054113 A1 | | 3/2004 | Benz et al. | |
| 2004/0054210 A1 | | 3/2004 | Benz et al. | |

FOREIGN PATENT DOCUMENTS

| | | | |
|---|---|---|---|
| EP | 0 661 332 | * | 7/1995 |
| EP | 0 821 973 A3 | | 2/1998 |
| EP | 0 821 973 A2 | | 2/1998 |
| EP | 0 940 405 | * | 9/1999 |
| EP | 0 953 622 | | 11/1999 |
| GB | 2111067 | | 6/1983 |
| JP | 2002128856 | * | 5/2002 |
| WO | WO 91/11468 A1 | | 8/1991 |
| WO | WO 97/00293 A1 | | 1/1997 |
| WO | WO9702305 | | 1/1997 |
| WO | WO 97/02305 | | 1/1997 |
| WO | 97/16467 | * | 5/1997 |
| WO | WO 998/05701 | | 2/1998 |
| WO | WO 98/50086 | * | 11/1998 |
| WO | WO 98/54242 | | 12/1998 |
| WO | WO 99/03863 | | 1/1999 |
| WO | WO 99/50327 | * | 10/1999 |
| WO | WO 00/64971 | * | 11/2000 |
| WO | WO 01/07499 | * | 2/2001 |
| WO | WO02053612 | | 7/2002 |

OTHER PUBLICATIONS

Bielawski et al.,, Polymer, 2001;42:4939.
Blackwell et al.,, J. Am. Chem. Soc., 2000:122:58.
Gibson et al.,, Macromolecules, 2000;33:655.
Hillmyer et al.,, Macromolecules; 1993;26:872.
Hillmyer et al.,, Macromolecules, 1997;30:718.
Hoffman et al.,, Clin. Mater., 1993; 13(1–4):95–100.
Marmon et al.,, Macromolecules, 1995; 28:2602.
Marmo et al.,, Macromolecules, 1993;26:2137.
Maughon et al.,, Macromolecules, 2000;33:1929.
Odian, third ed.; John Wiley & Sons, Inc., New York, NY, 1991.
Schwendeman et al.,, Polymer Preprints, 2002; 43(1):280.
Shaffer et al.,, Macromolecules, 1998; 31:5145–5147.
Smith et al.,, Macromolecules, 2000;33:3781–3794.

(Continued)

*Primary Examiner*—Rachel Gorr
(74) *Attorney, Agent, or Firm*—Mueting, Raasch and Gebhardt, P.A.

(57) ABSTRACT

Compounds that include diorgano groups having quaternary carbons and optionally urethane groups, urea groups, or combinations thereof (i.e., polyurethanes, polyureas, or polyurethane-ureas), as well as materials and methods for making such compounds.

61 Claims, 3 Drawing Sheets

OTHER PUBLICATIONS

Speckhard et al.,, Polymer, 1985;26:55–69.

Speckhard et al.,, Polymer, 1985;26:70–78.

Wu et al.,, Macromolecules, 1995;28:3502–3508.

Coury et al.,, Technomic Publishing Co., Lancaster, PA (1984) 9, pp 130–168; edited by Kurt C. Frisch and Daniel Klempner.

J.P. Kennedy et al., Hanser Publishers, 1992. pp 192, Practice: New Products and Processes, 111.2.2.

Schwendeman et al., Polymer Preprints, 43(1), p. 282 (2002).

Speckhard et al., Rubber Chemistry Technology, 59, 405–481 (1986).

Schwendeman, et al., Gem–Dimethyl Branching in ADMET Polyethlene, Abstract from poster presented at the International Symposium for Olefin Metathesis (ISOM), Cambridge, MA (Aug. 5–7, 2001).

Ishigure et al., Nuclear Magnetic Resonance Spectra of Isobutylene–Chlorotrifluoroethylene Copolymer. II. Intrepretation of Fluorine Resonances in Terms of Tetrads and Their Temperature Dependence., Polymer J. 1971 2(3):321–7, 1971.

Pinchuk et al., Polyurethane/Silicone Composites for Long Term Implant in the Human Body, 49th Annual Tech. Conf. B. Soc. Plast. Eng., pp.:1802–1804, 1991.

Pinchuk et al., The Use of Silicone/Polyurethane Graft Polymers as a Means of Eliminating Surface Cracking of Polyurethane Prostheses, J. Blomater. Appl., 3(2):260–296, 1998.

Pinchuk et al., Polyurethane/Silicone Composites as Materials for Long Term Implant in the Human Body, 22nd International SAMPE Tech. Conf., pp.:133–144, 1990.

\* cited by examiner n = 3

COMPOUNDS CONTAINING QUATERNARY CARBONS, MEDICAL DEVICES, AND METHODS

This application claims priority from U.S. provisional applications 60/332,695, filed Nov. 14, 2001 and 60/361,254 filed Mar. 1, 2002.

FIELD OF THE INVENTION

This invention relates to compounds containing quaternary carbons, preferably such compounds are polymers containing urethane and/or urea groups, particularly elastomers. Such materials are particularly useful as biomaterials in medical devices.

BACKGROUND OF THE INVENTION

The chemistry of polyurethanes and/or polyureas is extensive and well developed. Typically, polyurethanes and/or polyureas are made by a process in which a polyisocyanate is reacted with a molecule having at least two functional groups reactive with the polyisocyanate, such as a polyol or polyamine. The resulting polymer can be further reacted with a chain extender, such as a diol or diamine, for example. The polyol or polyamine is typically a polyester, polyether, or polycarbonate polyol or polyamine, for example.

Polyurethanes and/or polyureas can be tailored to produce a range of products from soft and flexible to hard and rigid. They can be extruded, injection molded, compression molded, and solution spun for example. Thus, polyurethanes and polyureas, particularly polyurethanes, are important biomedical polymers, and are used in implantable devices such as artificial hearts, cardiovascular catheters, pacemaker lead insulation, etc.

Commercially available polyurethanes used for implantable applications include BIOSPAN segmented polyurethanes, manufactured by Polymer Technology Group of Berkeley, Calif., PELLETHANE segmented polyurethanes, sold by Dow Chemical, Midland, Mich., and TECOFLEX segmented polyurethanes sold by Thermedics, Inc., Woburn, Mass. Polyurethanes are described in the article "Biomedical Uses of Polyurethanes," by Coury et al., in *Advances in Urethane Science and Technology*, 9, 130–168, edited by Kurt C. Frisch and Daniel Klempner, Technomic Publishing Co., Lancaster, Pa. (1984). Typically, polyether polyurethanes exhibit more biostability than polyester polyurethanes and polycarbonate polyurethanes, as these are more susceptible to hydrolysis. Thus, polyether polyurethanes are generally preferred biopolymers.

Polyether polyurethane elastomers, such as PELLETHANE 2363-80A (P80A) and 2363-55D (P55D), which are prepared from polytetramethylene ether glycol (PTMEG) and methylene bis(diisocyanatobenzene) (MDI) extended with 1,4-butanediol (BDO), are widely used for implantable cardiac pacing leads. Pacing leads are electrodes that carry stimuli to tissues and biologic signals back to implanted pulse generators. The use of polyether polyurethane elastomers as insulation on such leads has provided significant advantage over silicone rubber, primarily because of the higher tensile strength of the polyurethanes.

There is some problem, however, with biodegradation of polyether polyurethane insulation, which can cause failure. Polyether polyurethanes are susceptible to oxidation in the body, particularly in areas that are under stress. When oxidized, polyether polyurethane elastomers can lose strength and can form cracks, which might eventually breach the insulation. This, thereby, can allow bodily fluids to enter the lead and form a short between the lead wire and the implantable pulse generator (IPG). it is believed that the ether linkages degrade, perhaps due to metal ion catalyzed oxidative attack at stress points in the material.

One approach to solving this problem has been to coat the conductive wire of the lead. Another approach has been to add an antioxidant to the polyurethane. Yet another approach has been to develop new polyurethanes that are more resistant to oxidative attack. Such polyurethanes include only segments that are resistant to metal induced oxidation, such as hydrocarbon- and carbonate-containing segments. For example, polyurethanes that are substantially free of ether and ester linkages have been developed. This includes the segmented aliphatic polyurethanes of U.S. Pat. No. 4,873,308 (Coury et al.). Another approach has been to include a sacrificial moiety (preferably in the polymer backbone) that preferentially oxidizes relative to all other moieties in the polymer, which upon oxidation provides increased tensile strength relative to the polymer prior to oxidation. This is disclosed in U.S. Pat. Nos. 5,986,034 (DiDomenico et al.), 6,111,052 (DiDomenico et al.), and 6,149,678 (DiDomenico et al.).

Although such materials produce more stable implantable devices than polyether polyurethanes, there is still a need for biostable polymers, particularly polyurethanes suitable for use as insulation on pacing leads.

SUMMARY OF THE INVENTION

The present invention relates to compounds, preferably polymers, that include diorgano groups having quaternary carbons. Particularly preferred polymers include urethane groups, urea groups, or combinations thereof (i.e., polyurethanes, polyureas, or polyurethane-ureas). This includes materials and methods for making such compounds. Preferably, the polymer is a segmented polyurethane. Certain embodiments of the polymers of the present invention can be used as biomaterials in medical devices. The polymer is also preferably substantially free of ester, ether, and carbonate linkages.

The present invention provides a polymer, and a medical device incorporating such polymer, which includes a group of the formula:

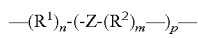

wherein: n=0 or 1; m=0 or 1; p=1–100,000; $R^1$ and $R^2$ are each independently a saturated or unsaturated aliphatic group, an aromatic group, or combinations thereof, optionally including heteroatoms, (preferably, the aromatic groups are within the backbone); and Z is —$C(R^3)_2$— wherein each $R^3$ is independently (i.e., they may be the same or different) a saturated or unsaturated aliphatic group, an aromatic group, or combinations thereof, optionally including heteroatoms, wherein the two $R^3$ groups within —$C(R^3)_2$— can be optionally joined to form a ring.

The present invention also provides a polymer, and a medical device that incorporates such polymer, wherein the polymer is prepared from a compound (typically a polymeric starting material) of the formula:

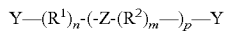

wherein: each Y is independently OH or $NR^4H$; n=0 or 1; m=0 or 1; p=1–2000; $R^1$ and $R^2$ are each independently a saturated or unsaturated aliphatic group, an aromatic group, or combinations thereof, optionally including heteroatoms (preferably, the aromatic groups are within the backbone); Z is $—C(R^3)_2—$ wherein each $R^3$ is independently a saturated or unsaturated aliphatic group, an aromatic group, or combinations thereof, optionally including heteroatoms, wherein the two $R^3$ groups within $—C(R^3)_2—$ can be optionally joined to form a ring; and each $R^4$ is independently H or a saturated or unsaturated aliphatic group, an aromatic group, or combinations thereof.

In certain preferred embodiments, the polymer is prepared from an isocyanate-containing compound and a compound of the formula:

$$Y—R^5—(—R^6\text{-}Z\text{-}R^7—)_q—R^8—Y$$

wherein: each Y is independently OH or $NH_2$; q=1–2000; Z is $—C(R^9)_2—$; $R^5$, $R^6$, $R^7$, and $R^8$ are each independently a straight chain alkylene group having 1–20 carbon atoms; and each $R^9$ is independently a straight chain alkyl group having 1–20 carbon atoms.

Also provided is a compound of the formula:

$$Y—(R^1)_n\text{-}(\text{-}Z\text{-}(R^2)_m—)_p—Y$$

wherein: each Y is independently OH, $NR^4H$, or protected forms thereof; n=0 or 1; m=0 or 1; p=1–2000; $R^1$ and $R^2$ are each independently a saturated or unsaturated aliphatic group, an aromatic group, or combinations thereof, optionally including heteroatoms, (preferably, the aromatic groups are within the backbone); Z is $—C(R^3)_2—$ wherein each $R^3$ is independently a saturated or unsaturated aliphatic group, an aromatic group, or combinations thereof, optionally including heteroatoms, wherein the two $R^3$ groups within $—C(R^3)_2—$ can be optionally joined to form a ring; and each $R^4$ is independently H or a saturated or unsaturated aliphatic group, an aromatic group, or combinations thereof.

In certain preferred embodiments of the present invention, there is a compound of the formula:

$$Y—R^5—(—R^6\text{-}Z\text{-}R^7—)_q—R^8—Y$$

wherein: each Y is independently OH or $NH_2$; q=1–2000; Z is $—C(R^9)_2—$; $R^5$, $R^6$, $R^7$, and $R^8$ are each independently a straight chain alkylene group having 1–20 carbon atoms; and each $R^9$ is independently a straight chain alkyl group having 1–20 carbon atoms.

It should be understood that in the formulas presented herein, the repeat units (e.g., $R^1$, $\text{-}Z\text{-}(R^2)_m—$, and $—R^6\text{-}Z\text{-}R^7—$) can vary within any one molecule.

As written, the formulas provided herein (for both the resultant polymers and the polymeric starting materials) encompass alternating, random, block, star block, segmented copolymers, and combinations thereof (e.g., wherein certain portions of the molecule are alternating and certain portions are random). With respect to star block copolymers, it should be understood that the polymeric segments described herein could form at least a part of one or more arms of the star, although the segment itself would not necessarily include the core branch point of the star.

Preferably, the polymers, and compounds used to make them, described herein have substantially no tertiary carbons in the main chain (i.e., backbone) of the molecules.

Methods of preparation of such polymers and compounds are also provided.

For example, a method of making a polymer that includes a urethane group, a urea group, or combinations thereof, and a group of the formula $—(R^1)_n\text{-}(\text{-}Z\text{-}(R^2)_m—)_p—$ includes combining an isocyanate-containing compound and a compound of the formula $Y—(R^1)_n\text{-}(\text{-}Z\text{-}(R^2)_m—)_p—Y$, which are described in greater detail herein. A method of making a polymer that includes a urethane group, a urea group, or combinations thereof, and a group of the formula $—C(R^9)_2—$ includes combining an isocyanate-containing compound and a compound of the formula $Y—R^5—(—R^6\text{-}Z\text{-}R^7—)_q—R^8—Y$, which are described in greater detail herein.

The present invention also provides a method of making a compound of the formula $Y—(R^1)_n\text{-}(\text{-}Z\text{-}(R^2)_m—)_p—Y$, described herein, which includes: polymerizing a diene compound having a quaternary carbon in the presence of a metathesis catalyst to form an intermediate polymer; depolymerizing the intermediate polymer in the presence of a chain transfer agent to form an unsaturated telechelic polymer; wherein the chain transfer agent includes protecting groups; and converting the unsaturated telechelic polymer to a compound of the formula $Y—(R^1)_n\text{-}(\text{-}Z\text{-}(R^2)_m—)_p—Y$. The step of polymerizing preferably includes polymerizing the diene compound in the presence of a chain extender and a metathesis catalyst to form an intermediate polymer. The step of converting the unsaturated telechelic polymer preferably includes: hydrogenating the unsaturated telechelic polymer to form a saturated telechelic polymer; and deprotecting the saturated telechelic polymer. Alternatively, the step of converting the unsaturated telechelic polymer preferably includes: deprotecting the unsaturated telechelic polymer; and hydrogenating the unsaturated telechelic polymer to form a saturated telechelic polymer.

The present invention also provides methods of making an alcohol and/or an amine that includes a quaternary carbon.

One method of making an alcohol and/or amine includes: polymerizing a compound having a quaternary carbon in the presence of a metathesis catalyst to form an intermediate polymer, wherein the compound having a quaternary carbon has the formula: $R^{10}HC=CH—(R^{11})_r\text{-}Z\text{-}(R^{12})_s—CH=CHR^{13}$ wherein: r=0 or 1; s=0 or 1; Z is $—C(R^3)_2—$, wherein each $R^3$ is independently a saturated aliphatic group, an aromatic group, or combinations thereof, optionally including heteroatoms, wherein the two $R^3$ groups within $—C(R^3)_2—$ can be optionally joined to form a ring; $R^{10}$ and $R^{13}$ are each independently hydrogen or straight chain, branched, or cyclic alkyl groups containing up to 6 carbon atoms; and $R^{11}$ and $R^{12}$ are each independently a saturated aliphatic group, an aromatic group, or combinations thereof, optionally including heteroatoms; depolymerizing the intermediate polymer in the presence of a chain transfer agent to form an unsaturated telechelic polymer; wherein the chain transfer agent includes protecting groups and has the formula: $Y—R^{17}—HC=CH—R^{18}—Y$ wherein: each Y is independently a protected form of OH or $NR^4H$; and $R^{17}$ and $R^{18}$ are each independently a saturated aliphatic group, an aromatic group, or an alcohol and/or an amine. Preferably, the step of polymerizing the compound having a quaternary carbon includes polymerizing the compound having a quaternary carbon in the presence of a chain extender and a metathesis catalyst to form an intermediate polymer. Preferably, the step of converting the unsaturated telechelic polymer to an alcohol and/or an amine includes: hydrogenating the unsaturated telechelic polymer to form a saturated telechelic polymer; and deprotecting the saturated telechelic polymer. Alternatively, the step of converting the unsaturated telechelic polymer to an alcohol and/or an amine preferably includes: deprotecting the unsaturated telechelic polymer; and hydrogenating the unsaturated telechelic polymer to form a saturated telechelic polymer.

Another method of making an alcohol and/or amine includes: polymerizing a compound having a quaternary carbon in the presence of a chain transfer agent and a metathesis catalyst to form an unsaturated telechelic polymer; wherein the compound having a quaternary carbon has the formula: $R^{10}HC=CH—(R^{11})_r-Z-(R^{12})_s—CH=CHR^{13}$, as described herein, wherein the chain transfer agent includes protecting groups and has the formula: $Y—R^{17}—HC=CH—R^{18}—Y$, as described herein; and converting the unsaturated telechelic polymer to an alcohol and/or an amine. Preferably, the step of polymerizing the compound having a quaternary carbon includes polymerizing the compound having a quaternary carbon in the presence of a chain transfer agent, a chain extender, and a metathesis catalyst to form an unsaturated telechelic polymer. Preferably, the step of converting the unsaturated telechelic polymer to an alcohol and/or an amine includes: hydrogenating the unsaturated telechelic polymer to form a saturated telechelic polymer; and deprotecting the saturated telechelic polymer. Alternatively, the step of converting the unsaturated telechelic polymer to an alcohol and/or an amine preferably includes: deprotecting the unsaturated telechelic polymer; and hydrogenating the unsaturated telechelic polymer to form a saturated telechelic polymer.

Another method of making an alcohol and/or amine includes: polymerizing a compound having a quaternary carbon in the presence of a metathesis catalyst to form an intermediate polymer, wherein the compound having a quaternary carbon has the formula: $R^{10}HC=CH—(R^{11})_r-Z-(R^{12})_s—CH=CHR^{13}$, as described herein; depolymerizing the intermediate polymer by reacting with a compound of the following formula to form an unsaturated telechelic polymer: $CH_2=CH—R^{21}—Y$ wherein each Y is independently a protected form of OH or $NR^4H$, and $R^{21}$ is a saturated aliphatic group, an aromatic group, or combinations thereof; and converting the unsaturated telechelic polymer to an alcohol and/or an amine. Preferably, the step of converting the unsaturated telechelic polymer to an alcohol and/or an amine includes: hydrogenating the unsaturated telechelic polymer to form a saturated telechelic polymer; and deprotecting the saturated telechelic polymer. Alternatively, the step of converting the unsaturated telechelic polymer to an alcohol and/or an amine preferably includes: deprotecting the unsaturated telechelic polymer; and hydrogenating the unsaturated telechelic polymer to form a saturated telechelic polymer.

As used herein, the terms "a," "an," "one or more," and "at least one" are used interchangeably.

As used herein, the term "aliphatic group" means a saturated or unsaturated linear (i.e., straight chain), cyclic (i.e., cycloaliphatic), or branched organic hydrocarbon group. This term is used to encompass alkyl (e.g., $—CH_3$, which is considered a "monovalent" group) (or alkylene if within a chain such as $—CH_2—$, which is considered a "divalent" group), alkenyl (or alkenylene if within a chain), and alkynyl (or alkynylene if within a chain) groups, for example. The term "alkyl group" means a saturated linear or branched hydrocarbon group including, for example, methyl, ethyl, isopropyl, t-butyl, heptyl, dodecyl, octadecyl, amyl, 2-ethylhexyl, and the like. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "aromatic group" or "aryl group" means a mono- or polynuclear aromatic organic hydrocarbon group. These hydrocarbon groups may be substituted with heteroatoms, which can be in the form of functional groups. The term "heteroatom" means an element other than carbon (e.g., nitrogen, oxygen, sulfur, chlorine, etc.).

As used herein, a "biomaterial" may be defined as a material that is substantially insoluble in body fluids and tissues and that is designed and constructed to be placed in or onto the body or to contact fluid or tissue of the body. Ideally, a biomaterial will not induce undesirable reactions in the body such as blood clotting, tissue death, tumor formation, allergic reaction, foreign body reaction (rejection) or inflammatory reaction; will have the physical properties such as strength, elasticity, permeability and flexibility required to function for the intended purpose; can be purified, fabricated and sterilized easily; and will substantially maintain its physical properties and function during the time that it remains implanted in or in contact with the body. A "biostable" material is one that is not broken down by the body, whereas a "biocompatible" material is one that is not rejected by the body.

As used herein, a "medical device" may be defined as a device that has surfaces that contact blood or other bodily tissues in the course of their operation. This can include, for example, extracorporeal devices for use in surgery such as blood oxygenators, blood pumps, blood sensors, tubing used to carry blood and the like which contact blood which is then returned to the patient. This can also include implantable devices such as vascular grafts, stents, electrical stimulation leads, heart valves, orthopedic devices, catheters, shunts, sensors, replacement devices for nucleus pulposus, cochlear or middle ear implants, intraocular lenses, and the like.

DETAILED DESCRIPTION OF ILLUSTRATIVE EMBODIMENTS OF THE INVENTION

Figure 1:
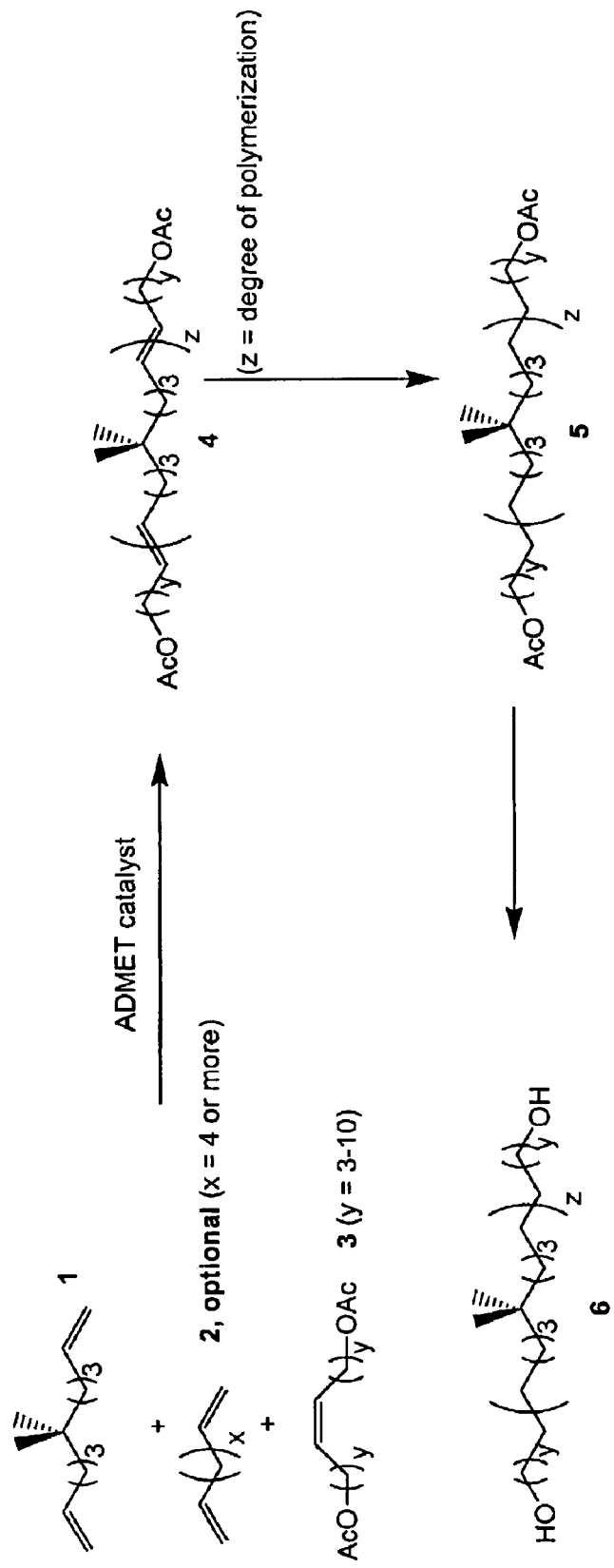
FIG. 1 is a schematic showing a preferred method of preparation of various compounds of the present invention.

The present invention provides polymers (preferably, segmented polyurethanes), compounds used to prepare such polymers (preferably, they form the soft segments of segmented polymers), and medical devices that include such polymers (preferably, biomaterials). Preferably, the polymers are generally resistant to oxidation and/or hydrolysis, particularly with respect to their backbones, as opposed to their side chains.

The polymers include one or more diorgano groups. These diorgano (e.g., gem-dialkyl) groups are of the general formula $—C(R^3)_2—$ wherein C is a quaternary carbon and each $R^3$ is independently (i.e., may be the same or different) a saturated or unsaturated aliphatic group, an aromatic group, or combinations thereof, optionally including heteroatoms (which may be in the chain of the organic group or pendant therefrom as in a functional group). Preferably, each $R^3$ is independently a straight chain alkyl group optionally including heteroatoms. Most preferably, each $R^3$ is independently a straight chain alkyl group without heteroatoms.

The polymers suitable for forming biomaterials for use in medical devices according to the present invention include quaternary carbons, and are preferably polyurethanes, polyureas, or polyurethane-ureas. These polymers can vary from hard and rigid to soft and flexible. Preferably, the polymers are elastomers. An "elastomer" is a polymer that is capable of being stretched to approximately twice its original length and retracting to approximately its original length upon release.

Polymers of the present invention can be homopolymers or copolymers, although preferably, they are random, alternating, block, star block, segmented copolymers, or combinations thereof. Most preferably, the polymers are segmented copolymers (i.e., containing a multiplicity of both hard and soft domains or segments on any polymer chain) and are comprised substantially of alternating relatively soft segments and relatively hard segments.

For segmented polymers either the hard or the soft segments, or both, include a diorgano moiety, thereby providing a polymer that has reduced susceptibility to oxidation and/or hydrolysis, at least with respect to the polymer backbone. As used herein, a "hard" segment is one that is either crystalline at use temperature or amorphous with a glass transition temperature above use temperature (i.e., glassy), and a "soft" segment is one that is amorphous with a glass transition temperature below use temperature (i.e., rubbery). A crystalline or glassy moiety or hard segment is one that adds considerable strength and higher modulus to the polymer. Similarly, a rubbery moiety or soft segment is one that adds flexibility and lower modulus, but may add strength particularly if it undergoes strain crystallization, for example. The random or alternating soft and hard segments are linked by urethane and/or urea groups and the polymers may be terminated by hydroxyl, amine, and/or isocyanate groups.

As used herein, a "crystalline" material or segment is one that has ordered domains. A "noncrystalline" material or segment is one that is amorphous (a noncrystalline material may be glassy or rubbery). A "strain crystallizing" material is one that forms ordered domains when a strain or mechanical force is applied.

An example of a medical device for which the polymers are particularly well suited is a medical electrical lead, such as a cardiac pacing lead, a neurostimulation lead, etc. Examples of such leads are disclosed, for example, in U.S. Pat. Nos. 5,040,544 (Lessar et al.), 5,375,609 (Molacek et al.), 5,480,421 (Otten), and 5,238,006 (Markowitz).

Polymers and Methods of Preparation

A wide variety of polymers are provided by the present invention. They can be homopolymers or alternating random, block, star block, or segmented copolymers (or combinations thereof), preferably they are copolymers (including terpolymers, tetrapolymers), that can include olefins, amides, esters, imides, epoxies, ureas, urethanes, carbonates, sulfones, ethers, acetals, phosphonates, and the like. These include moieties containing diorgano (preferably, gem-dialkyl) groups of the general formula —C(R)$_2$— wherein C is a quaternary carbon.

Such polymers can be prepared using a variety of techniques from polymerizable compounds (e.g., monomers, oligomers, or polymers) containing diorgano (preferably, gem-dialkyl) moieties of the general formula —C(R$^3$)$_2$— wherein C is a quaternary carbon. Such compounds include dienes, diols, diamines, or combinations thereof, for example.

Although certain preferred polymers are described herein, the polymers used to form the preferred biomaterials in the medical devices of the present invention can be a wide variety of polymers that include urethane groups, urea groups, or combinations thereof. Such polymers are prepared from isocyanate-containing compounds, such as polyisocyanates (preferably diisocyanates) and compounds having at least two functional groups reactive with the isocyanate groups, such as polyols and/or polyamines (preferably diols and/or diamines). Any of these reactants can include a diorgano moiety (preferably in the polymer backbone), although preferably a diorgano moiety is provided by the polyols and/or polyamines, particularly diols and/or diamines (including the diols or diamines of the dimer acid described below).

The presence of the diorgano moiety provides a polymer that is typically more resistant to oxidative and/or hydrolytic degradation but still has a relatively low glass transition temperature (Tg). Furthermore, preferably, both the hard and soft segments are themselves substantially ether-free, ester-free, and carbonate-free polyurethanes, polyureas, or combinations thereof.

Preferred polymers of the present invention include a group of the formula —(R$^1$)$_n$-(-Z-(R$^2$)$_m$—)$_p$— wherein -Z- is diorgano moiety —C(R$^3$)$_2$—. In one embodiment, particularly preferred polymers also include one or more urethane groups, urea groups, or combinations thereof (preferably, just urethane groups). In another embodiment, particularly preferred polymers are copolymers (i.e., prepared from two or more monomers, including terpolymers or tetrapolymers). Thus, the present invention provides polymers with these —(R$^1$)$_n$-(-Z-(R$^2$)$_m$—)$_p$— groups randomly distributed or ordered in blocks or segments.

Polymers of the present invention can be linear, branched, or crosslinked. This can be done using polyfunctional isocyanates or polyols (e.g., diols, triols, etc.) or using compounds having unsaturation or other functional groups (e.g., thiols) in one or more monomers with radiation crosslinking. Such methods are well known to those of skill in the art.

Preferably, polymers of the present invention (and the compounds used to make them) have substantially no tertiary carbons in the main chain (i.e., backbone).

In the group of the formula —(R$^1$)$_n$-(-Z-(R$^2$)$_m$—)$_p$—, n=0 or 1; m=0 or 1; p=1–100,000; R$^1$ and R$^2$ are each independently a saturated or unsaturated aliphatic group, an aromatic group, or combinations thereof, optionally including heteroatoms (which may be in the chain of the organic group or pendant therefrom), preferably with the proviso that the aromatic groups are within the backbone; and Z is a diorgano moiety —C(R$^3$)$_2$— wherein each R$^3$ is independently (i.e., may be the same or different) a saturated or unsaturated aliphatic group, an aromatic group, or combinations thereof, optionally including heteroatoms (which may be in the chain of the organic group or pendant therefrom), wherein the two R$^3$ groups within a —C(R$^3$)$_2$— moiety can be optionally joined to form a ring. It should be understood that the repeat unit -Z-(R$^2$)$_m$— can vary within any one molecule.

A preferred source of the group of the formula —(R$^1$)$_n$-(-Z-(R$^2$)$_m$—)$_p$— is a compound of the formula (Formula I):

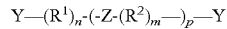

Y—(R$^1$)$_n$-(-Z-(R$^2$)$_m$—)$_p$—Y wherein: each Y is independently OH or NR$^4$H; n=0 or 1; m=0 or 1; p=1–2000; R$^1$ and R$^2$ are each independently a saturated or unsaturated aliphatic group, an aromatic group, or combinations thereof, optionally including heteroatoms (which may be in the chain of the organic group or pendant therefrom), preferably with the proviso that the aromatic groups are within the backbone; Z is —C(R$^3$)$_2$— wherein each R$^3$ is independently a saturated or unsaturated aliphatic group, an aromatic group, or combinations thereof, optionally including heteroatoms (which may be in the chain of the organic group or pendant therefrom), wherein the two R$^3$ groups within a —C(R$^3$)$_2$— moiety can be optionally joined to form a ring; and each R$^4$ is independently H or a saturated or unsaturated aliphatic group, an aromatic group, or combinations thereof.

It should be understood that any repeat unit can vary within any one molecule. That is, R$^6$ and R$^7$, for example, can be the same or different between repeat units in any one molecule. Similarly, $R^3$, as well as $R^9$, for example, can be the same or different between repeat units in any one molecule. Also, in addition to each $R^2$ being the same or different within each $Z(R^2)_m$ groups, the $Z(R^2)_m$ groups can be the same or different in any one molecule. Furthermore, each $R^1$ can be the same or different in any molecule.

The $R^3$ groups are selected such that the ultimate product (e.g., a segmented polyurethane polymer) has the following properties relative to a polymer without the diorgano (Z) moieties: reduced glass transition temperature (Tg) of the polymer; enhanced strength as a result of hydrogen bonding between the polymer chains; suppressed crystallization of soft segments at room temperature under zero strain; increased strain crystallization; greater ability to control phase separation for balancing elastomeric properties versus strength; greater ability to control melt rheology; and/or greater ability to modify the polymers using functional groups within the $R^3$ groups.

Although the diorgano moieties reduce the susceptibility of the compound of Formula I and the ultimate polymer to oxidation or hydrolysis, the $R^3$ groups could themselves be susceptible to oxidation or hydrolysis as long as the main chain (i.e., the backbone) is not generally susceptible to such reactions. Preferably, the $R^3$ groups are each independently a straight chain alkyl group, an aryl group, or combinations thereof. More preferably, the $R^3$ groups are each independently a straight chain alkyl group.

Optionally, the $R^3$ groups can include heteroatoms, such as nitrogen, oxygen, phosphorus, sulfur, and halogen. These could be in the backbone of the organic group or pendant therefrom as in the form of functional groups, as long as the polymer is generally resistant to oxidation and/or hydrolysis, particularly with respect to its backbone, as opposed to its side chains. Such functional groups include, for example, an alcohol, ether, acetoxy, ester, aldehyde, acrylate, amine, amide, imine, imide, and nitrile, whether they be protected or unprotected. Most preferably, each $R^3$ is independently a straight chain alkyl group without heteroatoms.

Preferably, $R^1$ and $R^2$ are each independently a straight chain alkylene group (e.g., a divalent aliphatic group such as $-CH_2-CH_2-$ and the like), an arylene group, or combinations thereof, preferably with the proviso that the aromatic groups are within the backbone. More preferably, $R^1$ and $R^2$ do not include tertiary carbon atoms in the main chain (i.e., backbone) of the molecule. Most preferably, $R^1$ and $R^2$ are each independently a straight chain alkylene group.

Preferably, each $R^4$ is independently hydrogen, a straight chain alkyl group, an aryl group, or combinations thereof. More preferably, each $R^4$ group is independently hydrogen or a straight chain alkyl group.

The $R^1$, $R^2$, $R^3$ and $R^4$ groups are selected such that the number average molecular weight of a compound of Formula I is no greater than about 100,000 grams per mole (g/mol or Daltons). Preferably, the molecular weight is about 1000 g/mol to about 1500 g/mol.

Preferably, $R^1$ and $R^2$ are each independently an organic group that includes at least one carbon atom, and more preferably at least two carbon atoms (this is particularly true for $R^2$). Preferably, $R^1$ and $R^2$ are each independently an organic group that includes no more than 100 carbon atoms, more preferably no more than 50 carbon atoms, and most preferably no more than 20 carbon atoms.

Preferably, $R^3$ is an organic group that includes at least one carbon atom. Preferably, $R^3$ is an organic group that includes no more than 100 carbon atoms, more preferably no more than 50 carbon atoms, and most preferably no more than 20 carbon atoms.

Preferably, $R^4$ is hydrogen or an organic group that includes at least one carbon atom. Preferably, $R^4$ is an organic group that includes no more than 100 carbon atoms, more preferably no more than 50 carbon atoms, even more preferably no more than 20 carbon atoms, and most preferably no more than 4 carbon atoms. Most preferably, $R^4$ is hydrogen.

The values for n, m, and p are average values. Preferably, at least one n or m is one. More preferably, both n and m are one. In increasing order of preference, p is 1–100,000, 1–50,000, 1–10,000, 1–5000, 1–2000, 1–1000, 1–500, 1–200, 1–100, 1–50, 1–20, 2–20, and 2–12.

Preferably, the Y groups are OH of $NH_2$. More preferably, the Y groups are both OH.

In Formula I, preferably at least one of the repeat units $-Z-(R^2)_m-$ is not a $-C(CH_3)_2CH_2-$ group when both Y groups are OH. Thus, preferably, the repeat unit $-Z-(R^2)_m-$ is not derived solely from isobutylene (in which $R^2$ is a $-CH_2-$ and each $R^3$ group is a $-CH_3$), particularly when both Y groups are OH. Rather, each $R^2$ group preferably has greater than one carbon atom (e.g., ethylene, propylene, butylene, etc.), even more preferably, greater than five carbon atoms, and most preferably, greater than eight carbon atoms. A polymer derived solely from isobutylene would not be expected to exhibit strain crystallization, although the polymers with longer $R^2$ groups would. Strain crystallization is desirable because the resultant polymer would have enhanced strength. That is, the mechanical properties of isobutylene-based polyurethanes are poor compared to conventional polyurethanes. Lack of soft segment crystallization and excessive phase separation under strain has been suggested for explanations for the unexpectedly low tensile properties. See, J. P. Kennedy et al., *Designed Polymers by Carbocationic Macromolecular Engineering Theory and Practice*, Hanser Publishers, 1992, page 192, and Speckhard et al., *Rubber Chem. Technol.*, 59, 405 (1986).

A preferred subset of Formula I are compounds of the formula (Formula II):

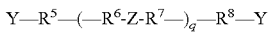

wherein: each Y is independently OH or $NH_2$; Z is $-C(R^9)_2-$; and $R^5$, $R^6$, $R^7$, and $R^8$ are each independently a straight chain alkylene group having 1–20 carbon atoms. Each $R^9$ is independently a straight chain alkyl group having 1–20 carbon atoms. Preferably, each $R^9$ is methyl. In such compounds, the repeat units $-R^6-Z-R^7-$ can vary within any one molecule. In increasing order of preference, q is 1–2000, 1–1000, 1–500, 1–200, 1–100, 1–50, 1–20, 2–20, and 2–12.

The polymers of the present invention can be prepared using standard techniques. Certain polymers can be made using one or more of the compounds of Formula I (preferably Formula II). Typically, a compound of Formula I is combined with an organic compound containing two or more groups capable of reacting with hydroxyl or amine groups. Other polymers can be made using the dienes of Formula III used to form these compounds, which are described in greater detail below.

For example, if Y in Formula I (or II) is an amine ($NR^4H$), one could react those amines with di-, tri- or poly(acids), di-, tri, or poly(acyl chlorides), or with cyclic amides (lactams) to form poly(amides). Alternatively, one could react those amines with di-, tri- or poly(anhydrides) to make poly (imides). Alternatively, one could react those amines with glycidyl-containing compounds to form epoxies.

If Y in Formula II (or II) is hydroxyl (OH), one could react those hydroxyl groups with di-, tri-, or poly(acids), di-, tri-, or poly(acyl chlorides), or with cyclic esters (lactones) to form poly(esters). Alternatively, one could react those hydroxyl groups with vinyl ether-containing compounds to make poly(acetals). Alternatively, one could react those hydroxyls with sodium hydroxide to form sodium salts, and further react those salts with phosgene to form poly (carbonates). Reacting those sodium salts with other alkyl halide containing moieties can lead to poly(sulfones) and poly(phosphates) and poly(phosphonates).

For the dienes of Formula III (below), one could react the terminal alkenes with di-, tri- or poly(amines) to make poly(imines). One could react the terminal alkenes with di-, tri-, or poly(alcohols) to make poly(ethers). Alternatively, one could convert the terminal alkenes to carbocations, anions or radicals and react these moieties with other alkenes to make polyolefin block copolymers.

Typically, the preferred urethane- and/or urea-containing polymers are made using polyisocyanates and one or more compounds of Formula I (preferably Formula II). It should be understood, however, that diols or diamines that do not contain such diorgano (Z) moieties can also be used to prepare the urethane- and/or urea-containing polymers of the present invention, as long as the resultant polymer includes at least some diorgano (Z) moieties either from diols or diamines or other reactants. Also, other polyols and/or polyamines can be used, including polyester, polyether, and polycarbonate polyols, for example, although such polyols are less preferred because they produce less biostable materials. Furthermore, the polyols and polyamines can be aliphatic (including cycloaliphatic) or aromatic, including heterocyclic, or combinations thereof.

Examples of suitable polyols (typically diols) include those commercially available under the trade designation POLYMEG and other polyethers such as polyethylene glycol and polypropylene oxide, polybutadiene diol, dimer diol (e.g., that commercially available under the trade designation DIMEROL (from Uniqema, New Castle, Del.), polyester-based diols such as those commercially available from STEPANPOL (from Stepan Corp., Northfield, Ill.), CAPA (a polycaprolactone diol from Solvay, Warrington, Cheshire, United Kingdom), TERATE (from Kosa, Houston, Tex.), poly(ethylene adipate) diol, poly(ethylene succinate) diol, poly(1,4-butanediol adipate) diol, poly (caprolactone) diol, poly(hexamethylene phthalate) diol, and poly(1,6-hexamethylene adipate) diol, as well as polycarbonate-based diols such as poly(hexamethylene carbonate) diol.

Other polyols can be used as chain extenders in the preparation of polymers, as is conventionally done in the preparation of polyurethanes, for example. Examples of suitable chain extenders include 1,10-decanediol, 1,1 2-dodecanediol, 9-hydroxymethyl octadecanol, cyclohexane-1,4-diol, cyclohexane-1,4-bis(methanol), cyclohexane-1,2-bis(methanol), ethylene glycol, diethylene glycol, 1,3-propylene glycol, dipropylene glycol, 1,2-propylene glycol, trimethylene glycol, 1,2-butylene glycol, 1,3-butanediol, 2,3-butanediol, 1,4-butanediol, 1,5-pentanediol, 1,6-hexanediol, 1,2-hexylene glycol, 1,2-cyclohexanediol, 2-butene-1,4-diol, 1,4-cyclohexanedimethanol, 2,4-dimethyl-2,4-pentanediol, 2-methyl-2,4-pentanediol, 1,2,4-butanetriol, 2-ethyl-2-(hydroxymethyl )-1,3-propanediol, glycerol, 2-(hydroxymethyl )-1,3-propanediol, neopentyl glycol, pentaerythritol, and the like.

Examples of suitable polyamines (typically diamines) include ethylenediamine, 1,4-diaminobutane, 1,10-diaminodecane, 1,12-diaminododecane, 1,8-diaminooctane, 1,2-diaminopropane, 1,3-diaminopropane, tris(2-aminoethyl)amine, lysine ethyl ester, and the like.

Examples of suitable mixed alcohols/amines include 5-amino-1-pentanol, 6-amino-1-hexanol, 4-amino-1-butanol, 4-aminophenethyl alcohol, ethanolamine, and the like.

Suitable isocyanate-containing compounds for preparation of polyurethanes, polyureas, or polyurethanes-ureas, are typically aliphatic, cycloaliphatic, aromatic, and heterocyclic (or combinations thereof) polyisocyanates. In addition to the isocyanate groups they can include other functional groups such as biuret, urea, allophanate, uretidine dione (i.e., isocyanate dimer), and isocyanurate, etc., that are typically used in biomaterials. Suitable examples of polyisocyanates include 4,4'-diisocyanatodiphenyl methane (MDI), 4,4'-diisocyanatodicyclohexyl methane (HMDI), cyclohexane-1,4-diisocyanate, cyclohexane-1,2-diisocyanate, isophorone diisocyanate, tolylene diisocyanates, naphthylene diisocyanates, benzene-1,4-diisocyanate, xylene diisocyanates, trans-1,4-cyclohexylene diisocyanate, 1,4-diisocyanatobutane, 1,12-diisocyanatododecane, 1,6-diisocyanatohexane, 1,5-diisocyanato-2-methylpentane, 4,4'-methylenebis(cyclohexyl isocyanate), 4,4'-methylenebis(2,6-diethyphenyl isocyanate), 4,4'-methylenebis(phenyl isocyanate), 1,3-phenylene diisocyanate, poly((phenyl isocyanate)-co-formaldehyde), tolylene-2,4-diisocyanate, tolylene-2,6-diisocyanate, dimer diisocyanate, as well as polyisocyanates available under the trade designations DESMODUR RC, DESMODUR RE, DESMODUR RFE, and DESMODUR RN from Bayer, and the like.

The relatively hard segments of the polymers of the present invention are preferably fabricated from short to medium chain diisocyanates and short to medium chain diols or diamines, all of which preferably have molecular weights of less than about 1000 g/mol. Appropriate short to medium chain diols, diamines, and diisocyanates include straight chain, branched, and cyclic aliphatics, although aromatics can also be used. Examples of diols and diamines useful in these more rigid segments include both the short and medium chain diols or diamines discussed above.

In addition to the polymers described herein, biomaterials of the invention can also include a variety of additives. These include, antioxidants, colorants, processing lubricants, stabilizers, imaging enhancers, fillers, and the like.

Starting Materials and Methods of Preparation

The novel compounds of Formula I and II above can be made by the synthetic route shown in FIG. 1 for preferred compounds. This typically involves a novel intermediate in which Y is a protected group such as an acetoxy (—OC(O) CH$_3$), a benzyl ether (—OCH$_2$phenyl), a tertiary butyl carbamate (—NR$^4$—C(O)-t-butyl), or a benzyl carbamate (—NR$^4$—C(O)OCH$_2$phenyl).

Thus, the present invention provides a compound of the formula (Formula I):

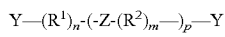

as described above.

Preferably, the present invention provides a compound of the formula (Formula II):

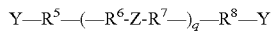

as described above.

Such compounds can be made starting with a diene compound having a quaternary carbon (i.e., a diorgano group referred to herein as Z or a —C(R$^3$)$_2$— group), a chain transfer agent, and optionally a chain extender. The quaternary carbon-containing diene compound is polymerized, optionally with a chain extender, in the presence of an ADMET (Acyclic Diene Metathesis) catalyst followed by incorporation of a chain transfer agent yielding an unsaturated telechelic polymer.

The two carbon-carbon double bonds of the diene compound can be either internal or terminal as long as they are separated by the Z group. Preferably, the diene is a compound of the formula (Formula III):

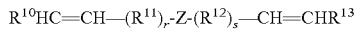

$$R^{10}HC=CH-(R^{11})_r-Z-(R^{12})_s-CH=CHR^{13}$$

wherein: r=0 or 1; s=0 or 1; Z is a —C(R$^3$)$_2$— group as defined above; $R^{10}$ and $R^{13}$ are each independently hydrogen or straight chain, branched, or cyclic alkyl groups containing up to 6 carbon atoms; and $R^{11}$ and $R^{12}$ are each independently a saturated aliphatic group, an aromatic group, or combinations thereof, optionally including heteroatoms, preferably with the proviso that the aromatic groups are within the chain. Preferably, using this synthetic procedure $R^3$ does not include unsaturated aliphatic groups, although it can include aromatic groups. The resultant polymers, however, could be subsequently modified to include aliphatic unsaturation.

Preferably, $R^{11}$ and $R^{12}$ are each independently a straight chain alkylene group, an arylene group, or combinations thereof, preferably with the proviso that the aromatic groups are within the chain. More preferably, $R^{11}$ and $R^{12}$ are each independently a straight chain alkylene group. Preferably, $R^{11}$ and $R^{12}$ are each independently an organic group that includes at least one carbon atom, and more preferably at least two carbon atoms. Preferably, $R^{11}$ and $R^{12}$ are each independently an organic group that includes no more than 100 carbon atoms, more preferably no more than 50 carbon atoms, and most preferably no more than 20 carbon atoms. Preferably, at least one of r or s is one. More preferably, both r and s are one. Most preferably, the quaternary carbon-containing starting material is Compound 1 in FIG. 1.

A chain extender can be optionally used to alter the spacing between the Z groups in the resultant polymer. This also has the added advantage of allowing for a broader range of glass transition temperatures (Tg's) than can normally be realized upon polymerizing one monomer. The chain extender is a diene wherein the two carbon-carbon double bonds are either internal or terminal. Preferably, it is a compound of the formula (Formula IV):

$$R^{14}HC=CH-R^{15}-CH=CHR^{16}$$

wherein: $R^{14}$ and $R^{16}$ are each independently hydrogen or straight chain, branched, or cyclic alkyl groups containing up to 6 carbon atoms; and $R^{15}$ is a saturated aliphatic group, an aromatic group, or combinations thereof, optionally including heteroatoms, preferably with the proviso that the aromatic groups are within the chain.

Preferably, $R^{15}$ is a straight chain alkylene group, an arylene group, or combinations thereof, preferably with the proviso that the aromatic groups are within the chain. More preferably, $R^{15}$ is a straight chain alkylene group. Preferably, $R^{15}$ is an organic group that includes at least one carbon atom, and more preferably at least two carbon atoms. Preferably, $R^{15}$ is an organic group that includes no more than 100 carbon atoms, more preferably no more than 50 carbon atoms, and most preferably no more than 20 carbon atoms. Most preferably, the chain extender starting material is Compound 2 in FIG. 1.

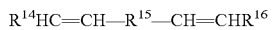

The chain transfer agent (CTA) includes protecting groups and is preferably a compound of the formula (Formula V):

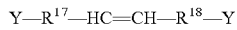

$$Y-R^{17}-HC=CH-R^{18}-Y$$

wherein: each Y is independently a protected form of an OH or an NR$^4$H group (e.g., wherein Y is an acetoxy, a benzyl ether, a tertiary butyl carbamate, or a benzyl carbamate); $R^{17}$ and $R^{18}$ are each independently a saturated aliphatic group, an aromatic group, or combinations thereof, preferably with the proviso that the aromatic groups are within the chain.

Preferably, $R^{17}$ and $R^{18}$ are each independently a straight chain alkylene group, an arylene group, or combinations thereof, preferably with the proviso that the aromatic groups are within the chain. More preferably, $R^{17}$ and $R^{18}$ are each independently a straight chain alkylene group. Preferably, $R^{17}$ and $R^{18}$ are each independently an organic group that includes at least one carbon atom, and more preferably at least two carbon atoms. Preferably, $R^{17}$ and $R^{18}$ are each independently an organic group that includes no more than 100 carbon atoms, more preferably no more than 50 carbon atoms, and most preferably no more than 20 carbon atoms. Examples of chain transfer agents include 1,8-diacetoxy-4-octene and 1,20-diacetoxyeicosa-10-ene. Most preferably, the chain transfer agent starting material is Compound 3 in FIG. 1 (1,8-diacetoxy-4-octene).

Alternatively, the chain transfer agent can include one alkene group and only one protected alcohol or amine. The alkene can be terminal or, if not terminal, it can include a relatively small alkyl substituent that forms a volatile compound under the metathesis conditions. An example of this type of chain transfer agent is 10-undecene-1-yl-acetate. Such a compound is generally of the formula (Formula VI):

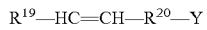

$$R^{19}-HC=CH-R^{20}-Y$$

wherein: Y is a protected form of an OH or an NR$^4$H group (e.g., wherein Y is an acetoxy, a benzyl ether, a tertiary butyl carbamate, or a benzyl carbamate); $R^{19}$ and $R^{20}$ are each independently a saturated aliphatic group, an aromatic group, or combinations thereof, preferably with the proviso that the aromatic groups are within the chain; $R^{19}$ can also be hydrogen. Preferably, $R^{19}$ is (C1–C6)alkyl group, and more preferably $R^{19}$ is H. If a compound of Formula IV is reacted with a compound of Formula III, the metathetic byproduct would be of the formula $R^{10}HC=CHR^{19}$, which should have sufficiently small $R^{10}$ and $R^{19}$ groups to be volatile under the conditions of the polymerization reaction.

Alternatively, the alcohol and/or amine groups can be introduced using a compound of the formula (Formula VII):

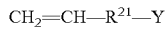

$$CH_2=CH-R^{21}-Y$$

wherein: each Y is independently a protected form of an OH or an NR$^4$H group (e.g., wherein Y is an acetoxy, a benzyl ether, a tertiary butyl carbamate, or a benzyl carbamate); $R^{21}$ is a saturated aliphatic group, an aromatic group, or combinations thereof, preferably with the proviso that the aromatic groups are within the chain. Preferably, $R^{21}$ is a straight chain alkylene group, an arylene group, or combinations thereof, preferably with the proviso that the aromatic groups are within the chain. More preferably, $R^{21}$ is a straight chain alkylene group. Preferably, $R^{21}$ is an organic group that includes at least one carbon atom, and more preferably at least two carbon atoms. Preferably, $R^{21}$ is an organic group that includes no more than 100 carbon atoms, more preferably no more than 50 carbon atoms, and most preferably no more than 20 carbon atoms.

Figure 2:
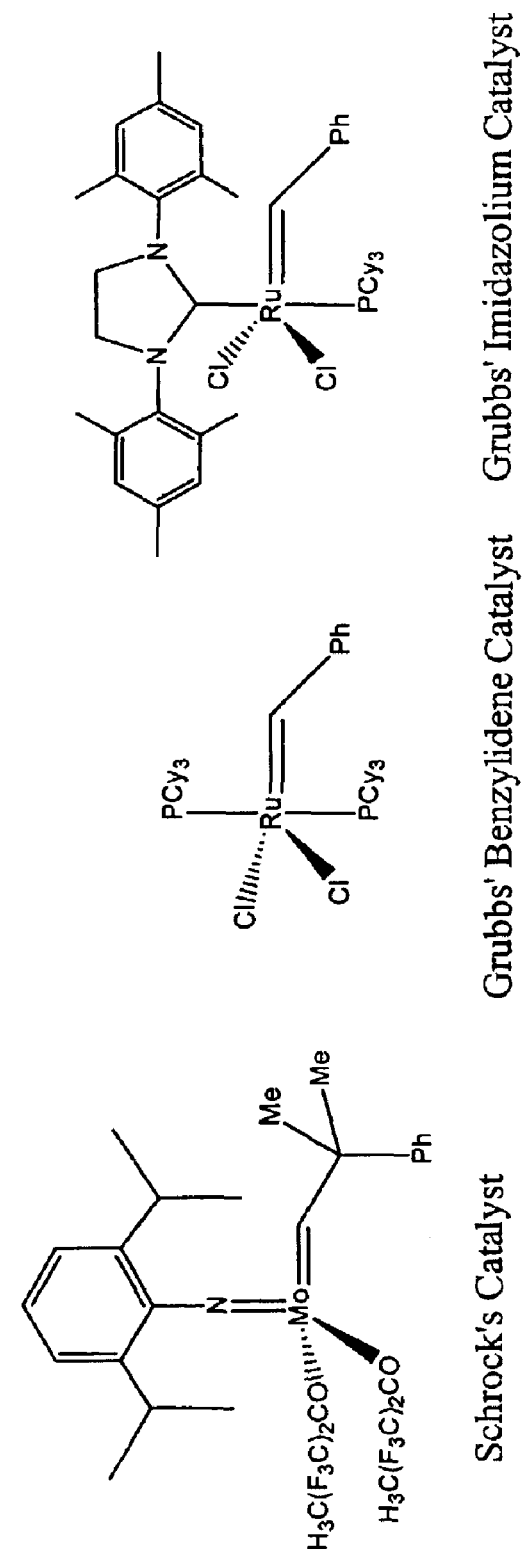
FIG. 2 lists examples of catalysts suitable for use in methods of the invention.

The ADMET catalyst can be any of a variety of catalysts capable of effecting metathesis polymerization. Examples include Schrock's molybdenum alkylidene catalyst, Grubbs' ruthenium benzylidene catalyst, and Grubbs' imidazolium catalyst ("Super-Grubbs"), as shown in FIG. 2.

Preferably, the quaternary carbon-containing diene compound is combined with an ADMET catalyst under conditions effective to cause polymerization to a high molecular weight intermediate (e.g., a number average molecular weight of about 10,000 g/mol to about $1 \times 10^6$ g/mol). Optionally, a chain extender can be added to the quaternary carbon-containing diene compound before the catalyst is added. Typically, conditions of this polymerization include reduced pressure (e.g., less than about 1.33 Pascals (Pa)) at a temperature of about 0° C. to about 100° C. (preferably, about 25° C. to about 60° C.) and a time of about 1 hour to about 10 days (preferably, about 48 hours to about 120 hours). The reduced pressure is desired to remove metathetic by-products and reduce the number of terminal olefins. This high molecular weight intermediate can be stored for later reaction if desired.

This high molecular weight intermediate is then combined with a chain transfer agent in the presence of the same or a different ADMET catalyst under conditions effective to depolymerize the high molecular weight intermediate and form an unsaturated telechelic polymer. Typically, such conditions include an inert atmosphere (e.g., argon) or under reduced pressure (e.g., less than about 1.33 Pascals) and a temperature of about 0° C. to about 100° C. (preferably, about 50° C. to 60° C.) and a time of about 1 hour to about 10 days (preferably, about 24 hours to about 96 hours). The amount of chain transfer agent controls the molecular weight of the unsaturated telechelic polymer. Optionally, this depolymerization reaction is carried out in an organic solvent (e.g., toluene) to reduce the viscosity.

Optionally, the unsaturated telechelic polymer could be formed in a one-step reaction in which the quaternary carbon-containing diene compound, optional chain extender, and a chain transfer agent are combined prior to the addition of the ADMET catalyst to the mixture. This may or may not be carried out in an organic solvent.

The unsaturated telechelic polymer is then subjected to a hydrogenation reaction. This is preferably carried out in the presence of a hydrogenation catalyst under conditions effective to form a fully saturated telechelic polymer. The hydrogenation catalyst is preferably palladium on activated carbon, but could be others well known in the art. Typically, such conditions include the use of a hydrogen pressure of about 1 psig (0.068 atmospheres, 6.89 Pa) to about 1000 psig (68 atmospheres, 6.89 MPa) (preferably, about 300 psig (20 atmospheres, 2.03 MPa) to about 500 psig (34 atmospheres, 3.45 MPa) and a temperature of about 0° C. to about 200° C. (preferably, about 60° C. to about 100° C.) and a time of about 1 hour to about 10 days (preferably, about 3 days to about 5 days).

Alternatively, the hydrogenation reaction can be carried out using para-toluenesulfonhydrazide in the presence of a base (typically, tributylamine) in a refluxing organic solvent such as xylene.

The saturated telechelic polymer is then deprotected using a reaction scheme specific to the protecting group used. For example, if the protecting group is an acetate, the polymer is hydrolyzed under conditions effective to convert the acetate end groups to hydroxyl groups. Typically, such conditions include the use of sodium methoxide in an organic solvent (e.g., methanol) at a temperature of about 0° C. to about 100° C. (preferably, about 0° C. to about 25° C.) and a time of about 1 minute to about 1 day (preferably, about 4 hours to about 1 day).

Alternatively, the unsaturated telechelic polymer could be deprotected prior to being hydrogenated to the saturated telechelic polymer.

The invention has been described with reference to various specific and preferred embodiments and will be further described by reference to the following detailed examples. It is understood, however, that there are many extensions, variations, and modification on the basic theme of the present invention beyond that shown in the examples and detailed description, which are within the spirit and scope of the present invention.

EXAMPLES

Instrumentation

All $^1$H NMR and $^{13}$C NMR spectra were recorded using either a Varian Associates Gemini 300 spectrometer or a JEOL Eclipse 400 spectrometer. Chemical shifts for $^1$H NMR were referenced to tetramethylsilane and those for $^{13}$C NMR were referenced to residual signals from $CDCl_3$ solvent. Reaction conversions and purity of products were monitored by chromatography. Gas chromatography was performed on a Shimadzu GC-17A gas chromatograph equipped with a Hewlett Packard HP-5 cross-linked 5% phenyl methyl siloxane column (length=25 meters (m), film thickness=0.33 micrometers (μm), internal diameter (ID)= 0.2 millimeters (mm)) and a flame ionization detector. Thin layer chromatography (TLC) was performed on WHATMAN aluminum backed, 250 mm silica gel coated plates, using mixtures of hexanes and ethyl acetate as the mobile phase. TLC plates were stained with phosphomolybdic acid (10%) in ethanol to see UV inactive products and impurities. High resolution mass spectra (HRMS) were obtained on a Finnegan 4500 gas chromatograph/mass spectrometer using the electron ionization (EI) mode. GPC data were obtained using a Waters Associates 6000A liquid chromatograph apparatus equipped with a HP refractive index detector. HPLC grade chloroform was used as the mobile phase, and a column bank consisting of two PLgel 5 μm MIXED-C columns (300 mm milliliter per minute (mL per minute) at 35° C. was maintained, and the instrument was calibrated using polystyrene standards from Polymer Laboratories. Elemental analyses were performed by Atlantic Microlabs Inc., Norcross, Ga. The tensile properties of polymer specimens were determined using a MTS Sintech 1/D tensile tester with extensometer with a crosshead speed of 12.7 cm per minute using a 45.5 kg (100 pound) load cell. The spinning band column used for distillations was the B/R 36/100A Automatic Distillation System with Vacuum Regulation, manufactured by B/R Instrument Corporation, Easton, Md. Polyurethane polymerizations were performed under an inert atmosphere using oven- or flame-dried glassware, with care used to maintain anhydrous conditions.

Materials

The Grubbs' imidazolium catalyst (FIG. 2) was synthesized following a literature procedure or purchased from Strem Chemicals, Inc. (Newburyport, Mass.). 5-Bromo-1-pentene was purchased from Aldrich and distilled from $CaH_2$ (38–40° C. at 12.4 kPa) prior to use. Propionic acid was purchased from Aldrich and distilled from anhydrous $Na_2SO_4$ (71–72° C. at 8.7 kPa), then redistilled from a few crystals of $KMnO_4$ prior to use. Diethyl ether and tetrahydrofuran (THF) were distilled from Na/K alloy using benzophenone as the indicator. Chloroform was distilled from $P_2O_5$, and hexamethylphosphoramide (HMPA) was distilled from $CaH_2$ prior to their use. One of the chain transfer agents (1,4-diacetoxy-2-butene) was purchased from Aldrich and distilled from CaH$_2$ (63° C. at 13 Pa) prior to use. The monomer for the new chain transfer agent (acetic acid 4-pentenyl ester) was purchased from TCI America (Portland, Oreg.) and used as received. The 10-undecen-1-yl acetate was purchased from Bedoukian Research, Incorporated (Danbury, Conn.) and used as received. QO POLYMEG 1000 was purchased from Penn Specialty Chemicals, Inc., Memphis, Tenn. The POLYMEG was dried under full oil pump vacuum at 100° C. prior to use. purchased from Bayer Corporation, Rosemount, Ill. and stored in a freezer until use. Anhydrous dioxane was purchased from Aldrich and was used as received. EPON 815c epoxy resin is available from Resolution Performance Products (Houston, Tex.). 1,4-Butanediol was produced by Mitsubishi Chemical Company (Japan). 1,9-Decadiene was purchased from Aldrich and distilled from calcium hydride prior to use, using the spinning band column described under "Instrumentation" above. All other reagents were obtained from Aldrich and used as received.

Example 1

Diene Synthesis

Figure 3:
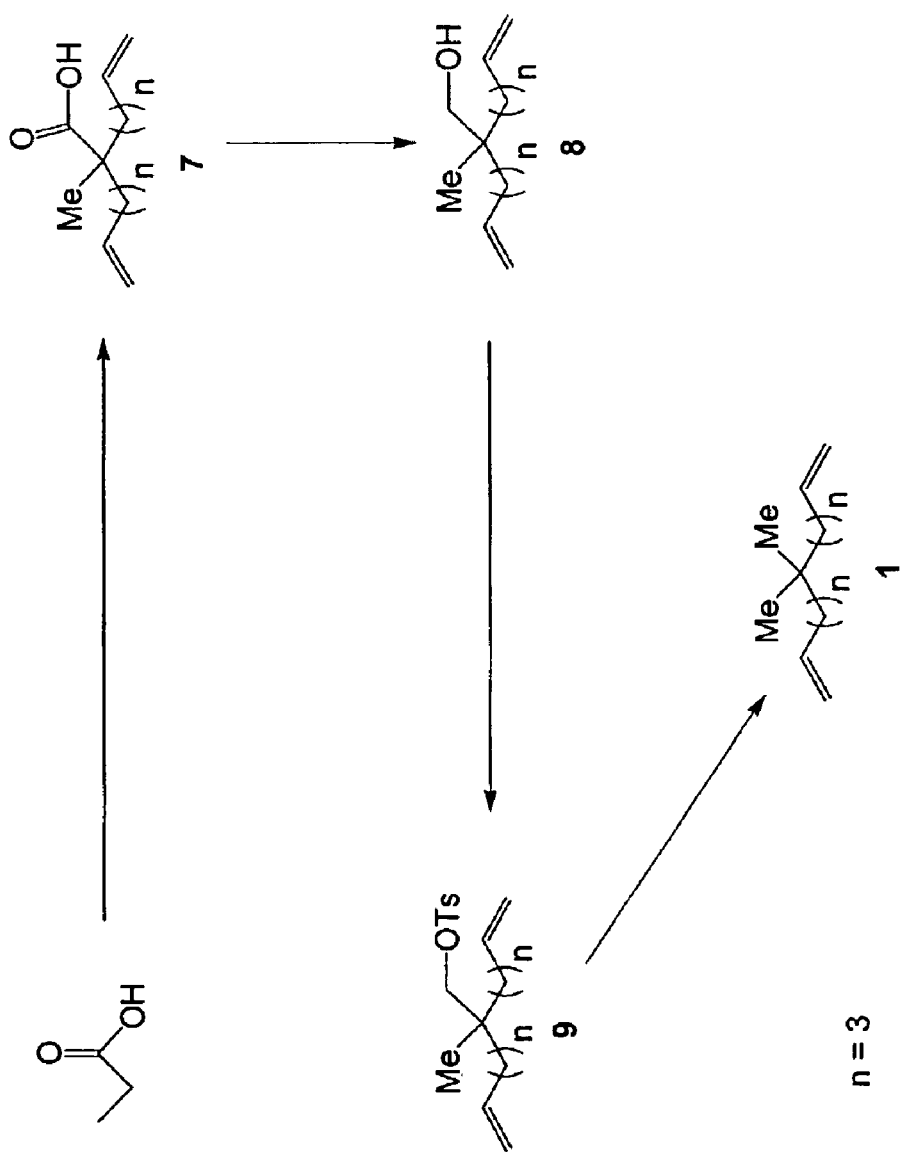
FIG. 3 is a schematic showing a preferred method of preparation of a diene suitable for use in the methods of the present invention.

Step 1: Dialkenylation of Propionic Acid. Synthesis and Characterization of 6-methyl-1,10-undecadiene-6-carboxylic Acid (Compound 7, FIG. 3)

One hundred thirty one mL (262 millimolar (mmol)) of a 2.0 M solution of lithium diisopropylamide (LDA) in THF (Aldrich) was placed in a flame-dried, argon-purged 1000 mL 3-neck round-bottomed flask equipped with a magnetic stir bar, 125 mL addition funnel, 250 mL addition funnel, and a condenser. The solution was cooled to −35° C. and 9.48 gram (g, 128 mmol) of propionic acid was added via syringe to the 125 mL addition funnel, followed by about 10 mL of THF. The propionic acid solution was added dropwise over about 50 minutes, and then the addition funnel was washed with THF. The reaction smoked considerably early on in the addition, and white salts formed. Approximately 25 mL of HMPA (about 1.1 equivalent to propionic acid) was added by syringe, and the mixture turned from a pale yellow to orange (salts still present). The mixture was allowed to warm to 10° C. over approximately 1 hour, followed by heating to 50° C. for 1.5 hours. The mixture was a reddish-orange with salts. The mixture was slowly chilled to −35° C. and 20.3 g (136 mmol) of 5-bromo-1-pentene was added to the 125 mL addition funnel via syringe. This was slowly dripped into the reaction mixture over 15 minutes. The mixture cleared after about 1 mL was added (colorless solution), then gradually turned yellowish with white salts. The mixture was slowly brought to 50° C. (salts dissolved and solution became pale yellow during heating) and was stirred for 2.5 hours. After 2.5 hours, the mixture had completely salted up. THF was slowly added by cannula with manual stirring until the salts had dissolved and the mixture became a pale yellow color again (about 200 mL of THF was added). The solution was again chilled to −35° C., and 65.5 mL (161 mmol) of the 2.0 M LDA solution was added to the reaction mixture dropwise from the 250 mL addition funnel over 40 minutes. The reaction mixture was allowed to warm to room temperature (solution turned more yellow), followed by heating to 50° C. for 1.5 hours (solution turned orange). The mixture was chilled to −35° C., and 21.4 g (144 mmol) of 5-bromo-1-pentene was slowly added from the 125 mL addition funnel over 25 minutes, and was then rinsed down with THF. The color lightened to yellow after the first few drops. The mixture was allowed to warm to room temperature, followed by heating to 50° C. for 12 hours (became pale yellow again).

After 12 hours, the mixture was allowed to cool to room temperature and then it was slowly poured over about 500 mL of ice in a 1000 mL beaker with stirring. Three molar HCl was added with stirring until all salts had dissolved. After concentration on a rotary evaporator, the quenched reaction mixture was extracted three times with 150 mL of diethyl ether. The combined organic layers were washed three times with 150 mL of 3 M hydrochloric acid (HCl), and then dried over anhydrous magnesium sulfate, gravity filtered, and evaporated under reduced pressure.

The percent yield was calculated to be about 70% based on the mass of the crude product and a GC analysis. The product was not purified before taking it on to the next step in this latest synthesis. If desired, the monoalkenylated product can be recovered by column chromatography using a 5:1 mixture of methylene chloride and ethyl acetate (or 74:25:1 hexanes:ethyl acetate:acetic acid) as the mobile phase.

The following spectral properties were observed: $^1$H NMR (CDCl$_3$): δ1.14 (s, 3H), 1.30–1.51 (m, 4H), 1.63 (dt, 4H), 2.04 (q, 4H), 4.93–5.04 (m, 4H), 5.72–5.83 (m, 2H), 11.95 (s, br, 1H); $^{13}$C NMR: δ21.07, 23.75, 34.10, 38.46, 45.61, 114.67, 138.46, 184.38; EI/HRMS: [M+1]$^+$ calcd. for C$_{13}$H$_{22}$O$_2$: 211.1698; found: 211.1698. Elemental analysis calcd. for C$_{13}$H$_{22}$O$_2$: 74.23 C, 10.55 H; found: 73.97 C, 10.59 H.

Step 2: Reduction of the Carboxylic Acid to the Alcohol. Synthesis and Characterization of 6-hydroxymethyl-6-methyl-1,10-undecadiene (Compound 8).

To an argon purged 1000 mL 3-neck flask equipped with a stir bar and condenser, 200 mL of dry diethyl ether and 12.0 g of the crude carboxylic acid mixture (about 82% dialkenylated and 18% monoalkenylated by GC analysis) from step 1 were added. Prior to addition, the carboxylic acid mixture had been left under vacuum for 12 hours to partially dry it. The solution was stirred for 5 minutes and cooled in an ice bath, before 140 mL of 1.0 M lithium aluminum hydride (LAH) in diethyl ether (Aldrich) was added slowly, in three portions, via syringe. Gas evolution was observed upon addition of LAH. The reaction mixture was allowed to warm to room temperature and stirred for approximately 20 hours.

After 20 hours, the mixture was slowly poured onto ice in a 1400 mL beaker. Vigorous evolution of gas was observed. Three normal (3N) HCl was added slowly until the salts dissolved. About 450 mL of 3N HCl was required. The aqueous layer was extracted three times with 100 mL of Et$_2$O. The combined ether layers were washed with two 100 mL portions of 3N HCl, once with 100 mL of saturated aqueous sodium bicarbonate, and once with de-ionized water. The organic layer was then dried over anhydrous magnesium sulfate, gravity filtered, and evaporated under reduced pressure.

The crude product was a strong smelling, viscous, clear oil, obtained in 94.3% yield. The two-component, alcohol product mixture was distilled at a pressure of 13 Pa. The monoalkenylated alcohol boiled at 41–43° C., and the desired diene alcohol boiled at 84–85° C. An isolated yield of 72.3% was obtained for the diene alchol, and its purity was confirmed by GC analysis.

The following spectral properties were observed: $^1$H NMR (CDCl$_3$): δ0.84 (s, 3H), 1.19–1.35 (m, 9H), 2.03 (q, 4H), 3.35 (d, 2H), 4.93–5.05 (m, 4H), 5.75–5.86 (m, 2H); $^{13}$C NMR (CDCl$_3$): δ21.83, 22.81, 34.57, 35.84, 37.21, 69.64, 114.43, 138.90; EI/HRMS: [M]$^+$ calcd. for C$_{13}$H$_{24}$O: 196.1827, found: 196.1829. Elemental analysis calcd. for C$_{13}$H$_{24}$O: 79.52 C, 12.33 H; found: 79.40 C, 12.36 H.

Step 3: Tosylation of the Alcohol. Synthesis and Characterization of 6-methyl-6-(p-toluenesulfonyl)methyl-1,10-undecadiene (Compound 9, FIG. 3)

To a flame dried, argon purged 500 mL 3-neck flask equipped with a stir bar, were added 100 mL of dry CHCl$_3$, via cannula, and 7.72 g (39.3 mmol) of the alcohol (Compound 8, FIG. 3) from step 2. After cooling the solution in an ice bath and stirring for 15 minutes, nine (9) mL (125 mmol) of dry pyridine was added via syringe. The reaction mixture was stirred for 30 minutes, and then toluenesulfonyl chloride was added in four 4 g portions (approximately 84 mmol) over a 30 minute period. The reaction mixture was allowed to warm to room temperature and stirred for 48 hours. The solution gradually became pale yellow.

The reaction mixture was poured over ice in a 1000 mL beaker, and 200 mL of 3N HCl was added slowly, with stirring. The mixture was placed in a separatory funnel and the CHCl$_3$ layer was drained. The aqueous layer was extracted twice more with a total of 100 mL of CHCl$_3$. The combined organic layers were washed twice with 100 mL of saturated aqueous potassium carbonate and twice with 100 mL of distilled water. The CHCl$_3$ layer was dried over magnesium sulfate, gravity filtered, and evaporated under reduced pressure. A yield of 21.8 g of crude yellow material was obtained. Analysis of the crude product using $^1$H and $^{13}$C NMR showed the presence of toluenesulfonic acid. The crude product was used in the next example without further purification.

The following spectral properties were observed: $^1$H NMR (CDCl$_3$): δ0.82 (s, 3H), 1.12–1.23 (m, 8H), 1.94 (q, 4H), 2.45 (s, 3H), 3.69 (s, 2H), 4.90–4.99 (m, 4H), 5.66–5.79 (m, 2H), 7.34 (d, 2H), 7.78 (d, 2H); $^{13}$C NMR (CDCl$_3$): δ21.73, 22.42, 34.24, 35.70, 36.33, 114.60, 127.89, 129.77, 132.75, 138.51, 144.64. The toluenesulfonic acid impurity has $^1$H NMR (CDCl$_3$) shifts at 2.49 (s, 3H), 7.41 (d, 2H), and 7.92 (d, 2H).

Step 4: Reduction of the Tosylate. Synthesis and Characterization of 6,6-dimethyl-1,10-undecadiene (Compound 1, FIG. 3)

To a flame dried, argon purged 500 mL 3-neck flask equipped with a condenser and stir bar, were added 80 mL of dry diethyl ether and 20.7 g of the crude tosylate (Compound 9, FIG. 3) from the previous step. The solution was chilled in an ice bath, and 175 mL of 1.0 M lithium aluminum hydride in Et$_2$O was slowly added, in four portions, via syringe. The reaction mixture immediately turned cloudy white. The mixture was allowed to warm to room temperature, and stirred for approximately 20 hours.

The reaction mixture was slowly poured over ice in a 1600 mL beaker, with stirring. Deionized water was added until frothing ceased. Then, 3N HCl was added until the white salt had completely dissolved. The aqueous layer was extracted three times with 100 mL of diethyl ether. The combined organic layers were washed twice with 100 mL of saturated aqueous potassium carbonate, twice with 3N HCl, twice more with 100 mL of saturated aqueous potassium carbonate, and once with 100 mL of distilled water. The colorless crude product was purified by flash column chromatography using silica gel 60 as the stationary phase and 100% hexanes as the mobile phase. Pure dimethyl diene (4.68 g) was obtained. The two-step yield (tosylation followed by reduction) was 66%, and the overall yield for all four steps was 27%. Before polymerization, the dimethyl diene was distilled from CaH$_2$ at 2.00 kPa into a 50 mL Schlenk flask, and stored under argon atmosphere. The boiling point at 2.00 kPa was 80–81.5° C.

The following spectral properties were observed: $^1$H NMR (CDCl$_3$): δ0.83 (s, 6H), 1.13–1.21 (dt, 4H), 1.25–1.35 (m, 4H), 2.01 (q, 4H), 4.91–5.04 (m, 4H), 5.75–5.88 (m, 2H); $^{13}$C NMR (CDCl$_3$): δ23.45, 27.25, 32.57, 34.70, 41.43, 114.16, 139.19; EI/HRMS: [M]$^+$ calcd. for C$_{13}$H$_{24}$: 180.1878, found: 180.1877. Elemental analysis calcd. for C$_{13}$H$_{24}$: 86.58 C, 13.42 H; found: 85.99 C, 13.26 H.

Example 2

Chain Transfer Agent Synthesis

The synthesis of 1,8-diacetoxy-4-octene was carried out by the dimerization of acetic acid 4-pentenyl ester using the Grubbs' benzylidene catalyst (FIG. 2). In an argon atmosphere dry box, 108 mg (0.131 mmol) of the Grubbs' benzylidene catalyst was added to a 100 mL round bottomed flask equipped with one dry ice/isopropanol condenser and one water condenser, each with a hose connector with a valve, and a magnetic stir bar. The apparatus was removed from the dry box and attached to a Schlenk line through the dry ice/isopropanol condenser. The flask was opened to argon after purging the hose. An oil bubbler was attached to the water condenser, but the valve was left closed. Then, 21.66 g (0.1690 mol) of acetic acid 4-pentenyl ester was added to the flask by syringe, and the flask was placed in a 47° C. oil bath. A small amount of bubbling was observed in the purple solution. The valve connected to the oil bubbler was opened to allow argon and ethylene byproduct to flow out continuously. After 30 minutes, the dry ice/isopropanol bath was filled, the bubbler valve was closed, and the pressure was reduced to 9.3 kPa. The solution bubbled vigorously as it degassed and then slowed to a constant rate. After 90 minutes at reduced pressure the bubbling had ceased and the solution was a purplish-brown. The reaction vessel was opened to air and left stirring overnight at 48° C. The crude product was 95% dimer (30% cis, 60% trans) by GC, and was now a black solution. It was exposed to a reduced pressure of 40 Pa for one hour to remove residual starting ester, and then the product was distilled over CaH$_2$ at 40 Pa (bp 111–113° C.) and stored in a Schlenk flask. The isolated product weighed 12.2 g, with a yield of 63%.

Example 3

Telechelic Diol Polymer Synthesis

Step 1: ADMET Polymerization/Depolymerization of 6,6-dimethyl-1,10-undecadiene (Compound 1, FIG. 1) with 1,8-diacetoxy-4-octene as the chain transfer agent (CTA) (Compound 3, y=3, FIG. 1) Using the Grubbs' Imidazolium Catalyst to Give the Unsaturated Telechelic Diacetate Polymer (Compound 4, FIG. 1)

In an argon atmosphere dry box, 6.162 g (34.17 mmol) of the dry, degassed gem-dimethyl diene monomer (1) was placed in a 100 mL round bottom flask equipped with a large TEFLON magnetic stir bar. About 63 mg (460:1 monomer to catalyst ratio) of the Grubbs' imidazolium catalyst was added to the flask, and a valve adapter was attached to the flask in the closed position. The reaction vessel was removed from the glove box and immediately attached to a Schlenk line, where the valve adapter was flame dried under vacuum. The mixture was stirred slowly in a 46° C. oil bath (only about ⅓ of the liquid monomer level was immersed) and was opened to the vacuum line for 1–2 seconds. Vacuum was applied every 5–15 minutes for 1–2 seconds to control the intensity of bubbling for the next 12 hours. By then, the bubbling had slowed and the orange-brown mixture had become viscous enough to leave open to the vacuum line. After 10 minutes of full vacuum, the pressure was at 7 Pa, and the solution was bubbling steadily. After 4 hours the bubbling had slowed and the mixture was more viscous, so the temperature was increased to about 60° C. Over the next 24 hours the pressure gradually decreased to 0.67 Pa and the bubbling slowed. By that time the mixture was very viscous and difficult to stir, so the diffusion pump was turned on to reduce the pressure further (about 0.4 Pa). There was still an occasional bubble. After another 42 hours of reaction, no bubbles were observed, so the reaction vessel was sealed and taken into the dry box.

In the argon atmosphere dry box, 1.112 g (4.871 mmol, or 7:1 monomer to chain transfer agent ratio) of 1,8-diacetoxy-4-octene was added to the reaction vessel. About 2 mL of dry, degassed toluene was added and a condenser with two valve adapters was attached (for argon in and out). The reaction vessel was removed from the dry box and attached to a Schlenk line. The connector hose was put under vacuum and backfilled with argon three times. To dissolve the polymer and allow easy stirring, the mixture was heated to 60° C. and stirred with a large U-shaped magnet. Once loosened, the stir bar spun freely. The reaction vessel was then opened to the argon line and bubbler, and placed in a 60° C. oil bath. No bubbles were observed in the orange/brown solution. The solution gradually became less viscous over 72 hours, at which time it was removed from the oil bath and the reaction was quenched by exposure to air. Upon exposure to air for several hours, the mixture turned from orange/brown to black/brown. Finally, the solvent was removed under reduced pressure (27 Pa) and 5.959 g of polymer (4) was obtained (95% yield).

The $^1$H NMR spectrum (run in CDCl$_3$) showed that no terminal olefinic resonances were observed at 4.9 ppm and 5.8 ppm, indicating that the polymer is perfectly bifunctional within NMR detection limits. Integration of the peaks indicates a number average molecular weight of about 1340 grams per mole (7.3 repeat units on average).

Step 2: Hydrogenation of the Unsaturated Telechelic Diacetate Polymer (Compound 4, FIG. 1) to the Saturated Telechelic Diacetate Polymer (Compound 5, FIG. 1)

Polymer 4 (5.96 g) was dissolved in approximately 200 mL of toluene in the 450 mL glass liner for a Parr high pressure reactor. About 1.0 g of 10% palladium on activated carbon was added and the reactor was sealed. The reaction vessel was charged with 500 pounds per square inch (psi) (34 atmospheres) of ultra high purity hydrogen (grade 5), and the mixture was stirred at 100 revolutions per minute (rpm) and heated to 80° C. During the 5-day reaction period the reactor had to be re-pressurized with hydrogen several times.

After 5 days the mixture was allowed to cool to room temperature and the pressure was released. The reaction mixture was filtered through a short pad of silica gel (5.7 centimeter (cm) in a 10 cm diameter column) using a ratio of 75:25 of toluene and ethyl acetate as the mobile phase. This column removes both the imidazolium Grubbs and Pd/C catalysts. About 6.28 g of the saturated acetoxytelechelic polymer (Compound 5, FIG. 1) was obtained after heating to 50° C. under reduced pressure, but $^1$H NMR showed that a small quantity of toluene solvent remained. Analysis of the integrals in the $^1$H NMR spectrum indicated a number average molecular weight of about 1300 grams per mole (6.9 repeat units on average). This spectrum also showed that the polymer was quantitatively hydrogenated within detection limits (no olefin resonances were detected at 5.4 ppm).

Step 3: Hydrolysis of the Telechelic Diacetate Polymer (Compound 5, FIG. 1) to the Target Telechelic Hydrocarbon Diol (Compound 6, FIG. 1)

Under an argon atmosphere, about 6.28 g of polymer (Compound 5, FIG. 1) was dissolved in 100 mL of dry diethyl ether in a 1000 mL round bottomed flask, equipped with a condenser and magnetic stir bar. The solution was chilled in an ice bath and 140 mL (10 equivalents to acetate groups) of an ice chilled 0.7 M solution of sodium methoxide in dry methanol was added (5.3 g NaOMe in 140 mL of methanol). The mixture was stirred and allowed to warm to room temperature overnight. When the stirring was stopped, the mixture settled into two layers. A colorless liquid (the polymer) settled on the bottom, and on top was a yellowish solution. The solvents were removed using a rotary evaporator, and a yellowish polymer and salt mixture remained. About 50 mL of diethyl ether was added and the polymer partially dissolved. The polymer dissolved upon the addition 50 mL of 1.0 M was yellow. The mixture was poured into a separatory funnel, along with two 10 mL washings of 1.0 M HCl and three 15 mL diethyl ether washings of the flask. The separatory funnel was shaken and vented several times and the aqueous layer was drained. The aqueous layer was basic to litmus paper (pH 11+). The organic layer was saved and the aqueous layer was washed twice with 50 mL of diethyl ether. The three organic layers were combined and washed twice with 10 mL of 1.0 M HCl (washings were pH 1) and once with 50 mL of deionized water. The organic layer was then dried over MgSO$_4$, filtered, and then evaporated under reduced pressure, yielding a colorless viscous liquid.

After drying on a vacuum line at 40° C., the telechelic gem-dimethyl diol (Compound 6, FIG. 1) weighed 5.2 g for an overall percent yield of 87%. The $^1$H NMR spectrum showed a molecular weight of about 1200 grams per mole (6.9 repeat units on average). The $^1$H NMR spectrum also indicated that the end groups of polymer 5 were quantitatively hydrolyzed and that the hydroxytelechelic hydrocarbon polymer is perfectly difunctional within detection limits. The characteristic acetate signals due to the methyl group (2.05 ppm) and the methylene adjacent to the acetate (4.05 ppm) were not present.

Example 4

Synthesis of a Polyurethane Containing a Soft Segment Featuring Gem-Dimethyl Substituents The soft segment dialcohol containing gem-dimethyl substituents (Compound 6, FIG. 1) was transferred in dioxane solvent to a 100 milliliter round bottom flask. After rotary evaporation for 5 hours at 60° C. under oil pump vacuum, the flask containing the clear, colorless, viscous liquid diol (4.92 g, 0.0082 equivalents (as determined by proton NMR)) was transferred to a nitrogen-purged glovebox. Then 0.13 g 1,4-butanediol (0.00286 equivalents) was added, followed by dilution with 60 g anhydrous dioxane. Magnetic stirring of the flask contents under nitrogen was initiated before adding 1.57 g (0.01251 equivalents) freshly distilled, molten 4,4'-methylenebis(phenyl isocyanate).

The clear, colorless solution was stirred magnetically under nitrogen. Heat was supplied with an electrically heated mantle. Temperature was recorded using an immersed stainless steel thermocouple and an electronic temperature controller. After the temperature was stabilized at 67° C., one drop (about 0.03 g) dibutyltin dilaurate catalyst was added. The exotherm of reaction peaked at 71°

C. Temperature was then maintained at 70° C. After 40 minutes, a drop of the flask contents was evaporated on a KBR plate and infrared spectroscopy was used to monitor the degree of reaction. Residual isocyanate was observed by absorbance at 2272 cm$^{-1}$. To complete reaction of all isocyanate, 1,4-butane diol was added dropwise in two increments of 0.06 and 0.02 g. At that point, IR analysis indicated absence of residual isocyanate. The calculated isocyanate/hydroxyl ratio based on theoretical equivalent weights was 1.00/1.00.

To isolate the resultant polymer, one hundred milliliters isopropyl alcohol was stirred in a one-liter Waring blender. The warm (approximately 55° C.) solution was poured into the running blender over a period of 2–3 minutes. The polymer precipitated as a discrete white powder. Additional isopropyl alcohol was added and the stirring was continued for five minutes. The precipitate was filtered using #41 "fast" WHATMAN paper filter in a Buechner funnel connected to a water-aspirated four-liter filter flask. The damp powder was transferred back to the Waring blender and stirred with 500 milliliters of methanol for five minutes. The filtration and stirring with methanol was repeated as above. The solution was filtered a final time and the powder dried in a 60° C. vacuum oven at oil pump vacuum overnight.

The final product was 5.43 g of a fluffy white powder, yielding 81.4% of the theoretical amount. The powder was molded into a 0.254 mm (10 mil film in a heated press at 180° C. The film was clear, bubble free and did not adhere to itself. Analytical data for the polymer is included in the Table below.

Example 5

Synthesis of an Epoxy Polymer

Six (6) grams of poly(1,1-dimethyl nonane) diamine of molecular weight 1100 g/mol (amine equivalent weight (275 g/eq) is combined with 2 grams of diethylene triamine (amine equivalent weight 21 g/eq). The amine mixture is placed in a 60° C. oven for one hour and mixed occasionally until a clear solution is formed. This mixture is added to 22 grams of EPON 815C epoxy resin, a mixture of 89% w/w diglycidyletherbisphenol A and 11% w/w of butyl glycidyl ether (epoxide equivalent weight 192 g/eq) that is also preheated to 60° C. The epoxy resin and amine mixture are mixed with a spatula until a clear solution is formed. This mixture is poured into a TEFLON-coated pan and cured in an oven at 100° C. for four hours. A solid epoxy is formed from this reaction.

Example 6

Synthesis of a POLYESTER-POLY(1,1-DIMETHYLNONANE) Block Copolymer

One gram of hydroxytelechelic diol 6 is placed in a dried 100 mL single-neck round-bottomed flask. To this flask is added 500 mg epsilon-caprolactone. The contents are warmed until well mixed. The flask is then cooled to room temperature. One drop of stannous octanoate is added to the mixture. A valved vacuum adapter is connected to the flask, and the flask is then degassed by application of vacuum. The valve is closed, and the flask is removed to a vacuum oven. The flask is maintained at 140° C. under vacuum for twelve hours. The flask contents are next dissolved in methylene chloride and then precipitated into cold methanol to remove residual epsilon-caprolactone.

Example 7

Synthesis of 6-ACETOXYMETHYL-6-METHYL-1,10-UNDECADIENE

Into a 100 mL round-bottom flask equipped with a magnetic spin bar and a glass stopper was added 6-hydroxymethyl-6-methyl-1,10-undecadiene (9.41 g, 48 mmol), glacial acetic acid (60.1 g, 1.0 mol) and scandium (III) triflate (1.23 g, 2.5 mmol). The mixture was stirred at ambient temperature for approximately 10 minutes and a colorless solution was obtained. The reaction mixture was stirred for an additional 24 hours at ambient temperature. The reaction mixture was then transferred into a 500 mL separatory funnel and diluted with 100 mL of deionized water. The solution was extracted with three 50 mL portions of methylene chloride. The combined methylene chloride extracts were washed with two 100 mL portions of deionized water, 100 mL of saturated sodium bicarbonate, 100 mL of brine and finally dried over anhydrous magnesium sulfate. The excess methylene chloride was removed with a rotary evaporator to afford a light oil. The oil was distilled under vacuum to afford 9.39 g of 6-acetoxymethyl-6-methyl-1,10-undecadiene (bp=66 to 71° C./8.7 Pa). The FTIR, $^{13}$C and $^1$H nmr were consistent with the proposed structure.

Example 8

Synthesis of 6-METHOXYMETHYL-6-METHYL-1,10-UNDECADIENE

Into a 500 mL 3-necked round-bottom flask equipped with a thermometer, 125 mL pressure equalizing funnel, and a glass stirring shaft with a TEFLON paddle attached to an air motor was added 6-hydroxymethyl-6-methyl-1,10-undecadiene (49.1 g, 0.25 mol), tetra-n-butylammonium iodide (0.5 g) and 100 mL of hexane. To the vigorously stirred solution (maximum rpm with the air motor) was added 50% sodium hydroxide solution (52.0 g, 0.65 mol). The two-phase reaction mixture was stirred vigorously for approximately 30 minutes and dimethyl sulfate (37.8 g, 0.30 mol) was added dropwise to the reaction mixture over a 40 to 45 minute interval, not allowing the temperature to exceed 45° C. The reaction mixture was stirred an additional three hours and 5 mL of 30% ammonium hydroxide solution was added and stirring was continued for 30 minutes.

Into the reaction flask was added 100 mL of deionized water and the entire contents of the flask was transferred into a 500 mL separatory funnel. The aqueous layer was separated and the hexane layer was washed with 100 mL of deionized water and dried over anhydrous sodium sulfate. The excess hexane was removed with a rotary evaporator to afford a light oil. Vacuum distillation of the oil afforded 19.3 g of 6-methoxymethyl-6-methyl-1,10-undecadiene (bp= 154–155° C./1.07 kPa). The FTIR, $^{13}$C and $^1$H nmr were consistent with the proposed structure.

Example 9

Stability Testing

The oxidative stability of the polyurethane synthesized in Example 4 was compared to that of three other polyurethanes. All three of the polyurethanes used as comparisons contained poly(tetramethyleneoxide) in the soft segment. The comparative polyurethane of Example 10 had the same molar ratio of soft segment diol, 1,4-butanediol, and 4,4'-methylenebis(phenyl isocyanate) as found in the polyurethane of Example 4, permitting a direct evaluation of the effect of substituting the gem-dimethyl-containing diol of Example 3 for the poly(tetramethyleneoxide) soft segment typically used in implanted polyurethanes. The comparative polyurethane of Example 11 was formulated using the same starting materials as in Example 10, but their ratio was selected to have a durometer identical to that of the polyurethane of Example 4, which was 90 on the Shore A scale. This permits a comparison based on physical properties, rather than formulation. The third comparison polyurethane was the commercially available PELLETHANE-2363-80A polyurethane. The PELLETHANE polyurethane is a standard of the medical industry for use in long-term implant applications, such as pacemaker leads, and is sold by the Dow Chemical Company, Midland, Mich. As noted in the Table, below, the PELLETHANE polyurethane had significantly higher molecular weight than the other polyurethanes, and also contained a commercial antioxidant package. This higher molecular weight and the antioxidant package would be expected to the other polyurethanes, which contained no antioxidants.

Polymer specimens were soaked in 1M silver nitrate and 1M ferric chloride to test their oxidative stability. The polymers were molded into 0.305 mm (12 mil) thick films and cut into test specimens with a die according to ASTM D638-5. These test specimens were then annealed at 60 for eight hours. Test specimens were stored at 70° C. for 8 weeks in each of these solutions. The specimens were tested after rinsing with deionized water, drying to a constant weight in a vacuum oven, and then allowing the moisture level of the specimen to equilibrate to ambient laboratory conditions. Tensile properties of the test specimens were determined using an MTS Sintech 1/D tensile tester with extensometer with a crosshead speed of 12.7 cm per minute using a 45.5 kg (100 pound) load cell. Retention of physical properties was determined by comparison of the tensile properties of the test specimens to the tensile properties of identical specimens stored at ambient laboratory conditions. This comparison is reported for various properties of interest as a percentage in the Table, below, as "Percent Retention". In the Table, below, "UTS" stands for ultimate tensile strength, "Elong." stands for elongation, "Modulus" refers to Young's modulus, and "Disint." means that the polymer specimen disintegrated under the test conditions. Also in the Table, below, $M_w$, refers to the weight-average molecular weight, $M_n$, refers to the number-average molecular weight. Molecular weights are reported in kilodaltons (kD) and were determined by gel permeation chromatography using polystyrene standards. In the Table, below, PDI refers to the polydispersivity index, which is defined as $M_w/M_n$.

polyurethane, respectively. This test demonstrated the superior oxidative resistance of the polyurethane of Example 4 compared to the other polyurethanes. The elongation of the polyurethane of Example 4 was also better retained than was found for the comparison polyurethanes. The Young's modulus of Example 4 after exposure to silver nitrate was 94% of the control value, while the polyurethane of Example 10 was significantly increased to 254% of its control value. This increase in modulus is not desirable in many medical device applications, such as the insulation for cardiac pacemaker leads. The retention of the Young's modulus of Example 11 was similar (but slightly less than) that of Example 4. The Young's modulus of PELLETHANE fell to 56% of its control value. This loss of modulus is also undesirable for medical device applications.

For the ferric chloride test solution, the results were even more striking, in which the polyurethanes of Examples 10 and 11 disintegrated in the ferric chloride solution. While the polyurethane of Example 4 retained 79% of its ultimate tensile strength, the ultimate tensile strength of the PELLETHANE polyurethane tested in ferric chloride fell to 63% of its control value. The elongation of the polyurethane of Example 4 fell slightly to 84% of its control value, while the elongation of the PELLETHANE polyurethane increased slightly to 104% of its control value. The modulus of the polyurethane of Example 4 exposed to ferric chloride rose slightly to 115% of the control value, while the modulus of the PELLETHANE polyurethane fell to 56% of its control value.

Overall, this data demonstrates the superior oxidative resistance of the polyurethane of Example 4 compared to that of polyurethanes formulated with poly (tetramethyleneoxide) soft segments. The polyurethane of Example 4 had better retention of ultimate tensile strength than any of the other polyurethanes, and also had retention of elongation and of Young's modulus that was better than or similar to that of the other polyurethanes.

Example 10

Synthesis of a Comparative Polyurethane with a Poly(Tetramethyleneoxide) Soft Segment To a dry 100-mL round-bottomed flask equipped with a magnetic stirring bar was added 5.60 g of POLYMEG-1000,

TABLE

Summary of polyurethane oxidation resistance testing.

| Polyurethane Formulation | Shore hardness | $M_w$ (kD) | $M_n$ (kD) | PDI | Test Solution | PERCENT RETENTION | | |
|---|---|---|---|---|---|---|---|---|
| | | | | | | UTS | Elong. | Modulus |
| Example 4 | 90A | 60.2 | 43.0 | 1.76 | AgNO$_3$ | 88 | 92 | 94 |
| | | | | | FeCl$_3$ | 79 | 84 | 115 |
| Example 10 | 75A | 74.4 | 43.0 | 1.72 | AgNO$_3$ | 17 | 16 | 254 |
| | | | | | FeCl$_3$ | Disint. | Disint. | Disint. |
| Example 11 | 90A | 118.0 | 43.8 | 2.83 | AgNO$_3$ | 13 | 28 | 91 |
| | | | | | FeCl$_3$ | Disint. | Disint. | Disint. |
| PELLETHANE | 85A | 154.0 | 75.6 | 2.05 | AgNO$_3$ | 13 | 66 | 56 |
| | | | | | FeCl$_3$ | 63 | 104 | 56 |

It can be seen from the data presented in the Table, above, that soaking the polyurethane of Example 4 in the silver nitrate solution reduced its ultimate tensile strength to 88% of the control value. In contrast, the other polyurethanes suffered a significantly larger decrease in ultimate tensile strength, to 17%, 13%, and 13% of their control values for the polyurethanes of Examples 10, 11, and PELLETHANE 0.20 g 1,4-butanediol, and anhydrous dioxane. A heating mantle was used to heat the reaction. The amount of dioxane used was calculated to give a final composition of 15% solids. Molten, freshly distilled 4,4'-methylenebis(phenyl isocyanate) (2.19 g) was added to the stirred solution and heating was initiated. The temperature was stabilized at 61° C. A small drop (approximately 0.003 g) of dibutyltin dilaurate was then added. The reaction mixture exothermed to 66° C. about two minutes after the addition. The reaction mixture was stirred for an additional 2.5 hours. At this time, 0.06 g 1,4-butanediol was added. After 35 minutes, the IR band due to isocyanate had reduced considerably and stabilized in size. The reaction mixture was cooled to room temperature and the polymer was precipitated by pouring the cooled reaction mixture into stirred isopropanol in a Waring blender. The resulting slurry was then vacuum filtered using a Buechner funnel with a paper filter. The precipitated polymer particles were returned to the blender and stirred with methanol. The polymer was again filtered and washed with methanol, and then filtered a final time. The polymer particles were dried overnight in a 50° C. vacuum oven at full oil pump vacuum, at which time the polymer weight was checked. There was no further weight loss from the sample upon further treatment in the vacuum oven. The yield of polymer was 77.9%. The polymer was molded into a 0.254 mm thick film, which was clear and free of bubbles. The molded film was tacky. This film was then submitted to the protocol described in Example 9.

Example 11

Synthesis of a Comparative Polyurethane with a Poly(Tetramethyleneoxide) Soft Segment To a dry 100-mL round-bottomed flask equipped with a magnetic stirring bar was added 5.61 g of POLYMEG-1000 and anhydrous dioxane. A heating mantle was used to heat the reaction. The amount of dioxane freshly distilled 4,4'-methylenebis(phenyl isocyanate) (2.93 g) was added to the stirred solution and heating was initiated. The temperature was stabilized at 70° C., at which time the solution was clear and of low viscosity. A small drop (approximately 0.003 g) of dibutyltin dilaurate was then added. The reaction mixture exothermed to 78° C. about two minutes after the addition. The reaction mixture was stirred for an additional three hours. Infrared analysis of the polymer residue created by evaporating a drop of the reaction mixture on a KBr plate showed the presence of a prominent band due to isocyanate. At this time, 0.42 g 1,4-butanediol was added. The reaction mixture exothermed to 74° C. over about five minutes. After 40 minutes, the IR band due to isocyanate had reduced considerably and stabilized. An additional 0.13 g of 1,4-butanediol was added, which again caused an exotherm to 74° C. over about five minutes. The solution was now much higher in viscosity. Forty five minutes after the final addition, the reaction mixture was cooled to room temperature. The polymer was precipitated by pouring the cooled reaction mixture into stirred isopropanol in a Waring blender. The resulting slurry was then vacuum filtered using a Buechner funnel with a paper filter. The precipitate polymer particles were returned to the blender and stirred with methanol. The polymer was again filtered and washed with methanol, and then filtered a final time. The polymer particles were dried overnight in a 50° C. vacuum oven at full oil pump vacuum. There was no further weight loss from the sample due to evaporating solvent. The polymer was molded into a 0.254 mm film, which was clear and free of bubbles. This film was then submitted to the protocol described in Example 9.

Example 12

Synthesis of a Hydroxytelechelic Copolymer Based on the Gem-Dimethyl Monomer and 1,9-DECADIENE Step 1: ADMET Copolymerization of Gem-Dimethyl Monomer and 1,9-DECADIENE A sample 1,9-decadiene was purified by distillation using a spinning band column. The fraction that distilled at 53.0–53.8° C. at 1.33 kPa was used. Inside an argon atmosphere glovebox, 30.57 g (0.17 mol) gem-dimethyl monomer (synthesized as in Example 1) and 23.49 g (0.17 mol) distilled 1,9-decadiene were magnetically stirred in an oven-dried 500 mL single-neck round-bottomed flask. To this mixture 0.65 g Grubbs' imidazolium catalyst was added and the flask was connected to a vacuum line through a port in the glovebox. A vacuum controller was used to maintain the pressure at 5.2 kPa, to prevent 1,9-decadiene from evaporating before polymerization occurred. The solution bubbled rapidly. The temperature within the glovebox was 33° C. After 1.5 hours, full vacuum was applied to the flask, and the pressure dropped to 670 Pa. The solution continued to bubble rapidly. After 18 hours of reaction time, the pressure was 33 Pa, the glovebox temperature was 37° C. and large bubbles were still forming. When the pressure decreased to 20 Pa, a diffusion pump was opened to the system to further reduce the pressure. After 24 hours of reaction time, the pressure was 13 Pa and many bubbles were still forming. After 90 hours reaction time, the solution was very viscous and difficult to stir. The pressure had decreased to 4 Pa and large bubbles were generated. After 5 days (120 hours) of reaction time, a heating mantle, thermocouple and temperature controller were used to increase the reaction temperature to 55° C., and the stir rate was also increased, due to the reduction in viscosity upon heating. The pressure changed from 4 Pa to 7 Pa and an increase in the rate of bubble production was observed. On the sixth day of the reaction (144 hours), the solution was very viscous and difficult to stir. The temperature was increased to 70° C. and held at this temperature for eighteen hours. At that time the reaction was terminated and the flask was removed from the glovebox. The solution was dark brown in color and extremely viscous. The solution was diluted in hexanes and transferred to a one-liter round-bottomed flask. Approximately 800 mL hexanes were used in the dilution and transfer. AMBERLITE IRC-718 ion exchange resin (54 grams) was added in batches of 10–20 grams over a course of three hours and slowly stirred. The solution was still brown in color and the AMBERLITE resin was filtered from the solution using a Buechner funnel and Whatman 40 filter paper. Black particles collected on the filter paper and the solution changed from dark brown to light brown. The collected AMBERLITE resin was rinsed with additional hexanes. The solution was transferred from the filter flask to a two-liter round-bottomed flask. A second treatment of AMBERLITE resin was added (35 g) and within half an hour, the solution was yellow in color. The AMBERLITE resin was then removed by filtration as before. The copolymer solution was then eluted through a column of 3.25 cm diameter containing 4 cm each silica gel and activated neutral aluminum oxide. Additional hexanes were used to complete the elution of the polymer (until no trace of polymer was visible when a few drops of eluent were evaporated on a watchglass). The hexanes were removed by rotary evaporation at reduced pressure, and the clear, colorless, viscous product was transferred to a 500 mL round-bottomed flask. The final weight of the collected copolymer was 23.44 g (44% yield). The copolymer was analyzed using FTIR and NMR. The absorbances observed by FTIR were: 2954, 2852, 1470, 1438, 1384, 1364, 1311, 1240, 1081, 965, and 731 cm$^{-1}$. The peaks observed by proton NMR were: 5.95 (m), 5.3(m), 4.95(m), 1.9(m), 1.25(m), 1.15(m), 0.8 (d) ppm with CDCl$_3$ as the reference. The molecular weight of the polymer was estimated from the proton NMR spectrum (based on the integrals of the internal double bond peak at 5.35 ppm and of the chain end double bond peak at 4.95 ppm) to be 105,000 g/mol. The NMR analysis showed that most of the mass loss was due to loss of 1,9-decadiene from the copolymer, which presumably cyclized to form the moderately volatile cyclooctene and evaporated from the polymerization reaction. The polymer was thus preferentially enriched with units derived from the gem-dimethyl monomer, which was estimated by NMR to comprise approximately 75% of the copolymer composition.

Step 2: Synthesis of an Acetoxytelechelic Copolymer by ADMET Depolymerization.

In a 500 mL single-neck round-bottomed flask, 10.55 g of the chain transfer agent 1,20-diacetoxyeicosa-10-ene (prepared according to the procedure of Example 14) was magnetically stirred into 23.44 g of the gem-dimethyl/1,9-decadiene copolymer synthesized above. The flask was transferred to an argon atmosphere glovebox, where 0.08 g Grubbs' imidazolium catalyst was added to the flask. Vacuum was then applied to the flask and the contents started to bubble rapidly. After a few minutes, the pressure stabilized around 19 Pa. The solution was pink and viscous. The temperature inside the glovebox was 38° C. After 21 hours, the solution was orange in color and appeared to be much less viscous. The pressure had decreased to 7 Pa. The diffusion pump was then opened to the system and the pressure decreased to 3 Pa. After an additional 42 hours, the pressure had not changed and no more bubbles were observed. The flask was taken out of the glovebox and about 20 g AMBERLITE IRC-718 resin were added. The mixture was stirred for one hour, at which point the color had lightened. The AMBERLITE resin was filtered from the solution using a Buechner funnel and Whatman 40 filter paper. The product was further purified by passage through a column of 3.25 cm diameter containing 4 cm each silica gel and activated neutral aluminum oxide, with hexanes used as the eluent. The hexanes were then removed by rotary evaporation at reduced pressure. The final weight of the product was 28.16 g (82% yield). The acetoxytelechelic copolymer was characterized by FTIR and NMR. The absorbances observed by FTIR were: 2860, 2854, 1744, 1467, 1437, 1385, 1364, 1306, 1237, 1038, 966, 723, 633, and 605 cm$^{-1}$. The peaks observed in the proton NMR spectrum were: 5.3(m), 4.0(t), 2.0(s), 1.94(m), 1.6(m), 1.2 (m), 1.1(m), and 0.81 ppm with CDCl$_3$ as the reference. No terminal vinyl end groups were observed in the proton NMR region 5.9–6.0 or 4.9–5.0, indicating the polymer was completely terminated with acetoxy groups.

Step 3: Deprotection of the Acetoxytelechelic Copolymer.

A 50 weight percent NaOH solution was made by dissolving 22.9 g NaOH in 22.9 g water. This solution was added to a one-liter round-bottomed flask containing the 28.16 g acetoxytelechelic copolymer synthesized above. Next, 2.31 g of the phase transfer catalyst ALIQUOT 336 was added to the flask. The solution was magnetically stirred for eighteen hours. At that time, a small amount of white precipitate was observed, and 200 mL hexanes were added to make the solution homogeneous. After 20.5 hours, a heating mantle and water condenser were attached to the flask and the solution was heated to reflux. The deprotection reaction was monitored by FTIR, with the endpoint determined by the disappearance of the acetoxy peak at 1744 cm$^{-1}$. After 2 hours at reflux (22.5 hours total reaction time) the IR peak at 1744 cm$^{-1}$ was gone. The two-phase solution was then transferred to a 20-L separatory funnel. Saturated NaCl solution and chloroform were added until the emulsion dissipated and the organic and aqueous layers became clearly distinguishable. The aqueous phase was drained from the funnel, and the remaining organic phase was rinsed several times with deionized water, until the water used to wash the organic phase was pH 7. The organic phase was transferred to an Erlenmeyer flask and dried using anhydrous magnesium sulfate. The magnesium sulfate was then filtered using a Buechner funnel with Whatman 40 filter paper. The hexanes were removed by rotary evaporation under reduced pressure. The result was 27.77 g of the hydroxytelechelic copolymer. The copolymeric diol was a viscous, pale yellow liquid. The polymer was characterized by FTIR and NMR spectroscopy. The absorbances observed by FTIR were: 2958, 2872, 2858, 1466, 1378, 1364, 966, and 724 cm$^{-1}$. The peaks observed in the proton NMR spectrum were: 5.3(m), 3.6 (t), 1.9(m), 1.27(m), 1.18(m), 1.13(m), and 0.81 ppm with CDCl$_3$ as the reference.

Step 4: Hydrogenation of the Hydroxytelechelic Copolymer

The copolymeric diol synthesized in the previous step was dissolved in toluene to give a solution that was 9.7% solids. This solution was placed in a Parr pressure reactor and hydrogenated for ten days at 4.14 MPa and 60° C. The catalyst used was 10% palladium on activated carbon, one gram used for the first eight days and an additional 0.13 g added for the last two days. The catalyst was filtered from the reaction mixture. Analysis of the resulting polymer using proton NMR showed a small residual peak in the alkene region due to incomplete hydrogenation of the sample, corresponding to about eight percent of the initial value.

Example 13

Synthesis of a Polyurethane Based on the Hydroxytelechelic Diol of Example 12

The hydroxytelechelic diol of Example 12 was dissolved in 300 mL hexanes and a portion of the solution was passed through a column of 3.25 cm diameter containing 4 cm silica gel, with additional hexanes used as the eluent. The hexanes were removed under reduced pressure using a rotary evaporator. The extremely viscous, yellow diol was transferred to an oven-dried 250-mL 3-neck round-bottomed flask using 100 mL hexanes in the transfer. The 3-neck flask was placed on a rotory evaporator, with care taken not to submerge the joints. The hexanes were then removed under reduced pressure. A total of 6.1 g of hydroxytelechelic diol remained in the flask. The flask was then transferred to a nitrogen atmosphere glovebox. A magnetic stirring bar and 87.3 g anhydrous dioxane were added to the flask and the solution was magnetically stirred. From a syringe with a 21 Gauge needle, 0.60 g 1,4-butanediol (BDO) was added dropwise. The flask was then outfitted with an electric heating mantle, thermocouple, temperature controller, and air condenser. The diol mixture in anhydrous dioxane was heated and stirred. The hydroxytelechelic diol dissolved when the temperature reached 35° C. The solution temperature was increased to 67° C. and held at that temperature before the 4,4'-methylenebis(phenyl isocyanate) (MDI) was added. A total of 2.9 g MDI was weighed into a small plastic weighing boat and then added to the dioxane solution. One drop of dibutyltin dilaurate catalyst (0.0028 g) was added from a syringe with a 26 Gauge needle. The reaction was monitored by FTIR. A drop of the reaction solution was spread on a single KBR plate and placed in a 60° C. vacuum oven under full vacuum for two minutes to remove the dioxane. The isocyanate peak at 2275 cm$^{-1}$ was initially very strong. The temperature was held at 67° C. for half an hour and then increased to 70° C. for the remainder of the reaction. After one hour, there was no change in the FTIR spectrum. Over the course of 3.5 hours, 0.384 g more BDO was added dropwise, with one drop equal to 0.008 g on average, until the isocyanate absorbance at 2275 cm$^{-1}$ was very weak. The resulting absorbances observed by FTIR were: 3328, 3123, 3039, 2926, 2853, 2278, 1902, 1702, 1597, 1534, 1468, 1437, 1414, 1384, 1363, 1311, 1233, 1110, 1080, 1019, 968, 915, 849, 817, 772, 720, 663, 611, 509 cm$^{-1}$. The polyurethane was precipitated from the dioxane solution using acetone. Half of the polymer solution was poured into a Waring blender containing 500 ml acetone. The polyurethane formed a white, flaky precipitate. The precipitate was filtered using a Buechner funnel with 41 WHATMAN filter paper. The procedure was repeated with the other half of the batch. The two precipitate batches were then combined in the blender with another 500 ml acetone. The mixture was stirred in the blender to extract additional dioxane, and the precipitate was again filtered as described above. The polyurethane was transferred from the Buechner funnel to a MYLAR weighing boat and stored in a vacuum oven at 60° C. under full oil pump vacuum for eighteen hours. The fluffy, white polymer weighed 5.6 g, a 57% yield.

The polyurethane was then pressed into a 0.25 mm thick film in a heated press at 190° C., producing a bubble-free film that was yellow in color. ASTM D-638 Type 5 tensile strength test samples were stamped out of the polyurethane sheet.

Tensile testing was performed following ASTM method D638-5 with ext. (rev. A) using six samples. The averaged results were: Ultimate Modulus=27.3 MPa; Toughness=34.7 MPa; Stress at Yield=6.66 MPa; Percent Strain at Yield= 25.7%.

Example 14

Synthesis of 1,20-DIACETOXYEICOSA-10-ENE by Metathetic Dimerization of 10-UNDECEN-1-YL Acetate A chromatography column with an outside diameter of 7.6 inches containing 15 cm activated neutral alumina was connected to a twelve-liter single-neck round-bottomed flask using an adapter with a vacuum adapter. The 10-undecen-1-yl acetate was purified by passage through the column directly into the flask with vacuum applied through the adapter. The flask was weighed to find that 4.82 kg had been transferred to it. The flask was placed in a heating mantle on a magnetic stirring plate. A magnetic stir bar was added to the flask, and a sparge tube attached to a ground glass joint was fitted to it. The stirred monomer was sparged for twenty hours, then 10.93 g of the Grubbs' benzylidene catalyst (FIG. 2) was added to the flask and the neck quickly capped with a 20 cm Vigreux column connected to a vacuum line through an adapter. The vacuum line comprised an oil pump and a diffusion pump. Vacuum was immediately applied, and after 45 minutes, the pressure inside the flask had dropped sufficiently that the diffusion pump could be opened to the system, which reduced the pressure inside the flask to 1.33 Pa, and further dropped to 0.67 Pa five hours after the start of the reaction. Six hours after the catalyst was added, the reaction started to solidify, and gentle heat was applied to keep the reaction a stirrable slurry. An hour after heating was initiated, the temperature measure by a thermocouple placed between the flask and the mantle was 47.2° C. The variac controlling the heating mantle was turned down slightly at this point. The cold trap in the vacuum line had to be emptied every few hours to remove the condensed ethylene. Ten hours after the reaction was started, the temperature was 38° C., and after a further 15 hours, was 41.5° C. At this time, the variac was again turned down slightly. The reaction mixture at this time was an intense burgundy-colored liquid (except where mixture thrown against the wall of the flask above the mantle had solidified) and the pressure inside the flask was 0.4 Pa. By measuring the volume of liquid ethylene collected, the reaction was estimated to be 75% complete at this point. The reaction was continued for 7 days, with the temperature measured between the flask and mantle maintained at 43–44° C. At this point, the variac was turned up and the temperature equilibrated at 55.7° C. After 12 hours, the variac was again turned up, and the temperature equilibrated at 63.5° C. After twelve hours at this final temperature, the reaction was terminated, the flask backfilled with nitrogen, and ten grams of Irganox 1010 was added. The reaction mixture was diluted 1:1 with hexanes and maintained under nitrogen. Then 480 g of AMBERLITE IRC-718 ion exchange resin (washed with deionized water and dried under vacuum) was added to the flask and an air-driven mechanical stirrer was used to stir the reaction overnight. The next day, a chromatography column 76 cm long and 7.6 cm in diameter was filled consecutively with 5 cm sand, 20 cm activated neutral alumina, 5 cm AMBERLITE resin (ground in a ball mill), and 5 cm sand. The column was attached to a three-neck 12-liter round-bottomed flask. Vacuum from a water aspirator was attached to the flask through an adapter. The solution was pumped into the column using a peristaltic pump. The filtered solution was pale amber. The residue in the reaction flask was washed with several portions of hexanes, which was also pumped into the column. The column was further eluted with hexanes until no appreciable product remained on the column. The solution was placed in a freezer overnight, where it became a solid crystalline mass. After standing at room temperature for 24 hours, there was a large lump of white crystals in a pale amber solution. The liquid was pumped from the flask and the white crystals were washed twice with a liter of hexanes, with the liquid from these washings also pumped from the flask. Then hexanes were added to the flask to give a total volume of about eleven liters and the flask was heated to dissolve the crystals. The resulting solution was much paler in color than the initial hexanes solution. It was allowed to stand overnight at room temperature, but no crystals precipitated. It was then put in a freezer overnight, which resulted in a solid mass. After standing at room temperature for about two hours, the massed had thawed sufficiently that it could be filtered in two portions using a paper filter in a large Buechner funnel. Each portion of crystals was washed with 500 mL of room-temperature hexanes. The crystals were placed in a PYREX dish and then placed under vacuum overnight to remove the remaining hexanes. A total of 640 g of white crystalline product was isolated (the remaining product of the reaction was also isolated and reserved for other uses). The product was recrystallized from hexanes before use. As expected, twelve peaks were observed by $^{13}$C NMR: δ171.3, 130.4, 64.7, 31.2, 29.7, 29.5, 29.4, 29.3, 29.1, 28.6, 25.9, 20.3 ppm. The peaks observed by proton NMR were: δ5.3 (t), 4.0 (t), 2.1 (s), 1.9 (m), 1.5 (m), 1.2 (m).

Example 15

Alternative Tosylation and Reduction to Produce 6, 6-DIMETHYL-1,10-UNDECADIENE

Step 1: Tosylation

Into an oven-dried nitrogen-purged one-liter 3-neck round-bottomed flask equipped with a nitrogen inlet and a magnetic stir bar was added 98.16 g of 6-hydroxymethyl-6-methyl-1,10-undecadiene and 300 mL chloroform. The solution was cooled to 5–15° C. with an ice bath and 48.5 mL pyridine (47.5 g) was added to the flask. The solution was stirred for about five minutes and p-toluenesulfonyl chloride (104.9 g) was added to the solution over a 15 minute interval. The solution was allowed to warm to ambient temperature and was stirred for about 72 hours. The light yellow reaction mixture was poured onto approximately 1.5 kg crushed ice, followed by the addition of 800 mL of 3N HCl. The two-phase system was transferred to a 3L separatory funnel and the chloroform layer was isolated. The aqueous layer was extracted with two 125 mL portions of chloroform. The combined chloroform extracts were washed sequentially with two 100 mL portions of saturated aqueous potassium carbonate, two 250 mL portions of de-ionized water, and 100 mL of brine. The chloroform solution was then dried over anhydrous magnesium sulfate. The chloroform was removed using a rotary evaporator to afford 165.95 g of a light yellow oil, which is 95% of the theoretical yield. The crude product was used in the following step with no further purification. Infrared analysis showed no bands due to hydroxyl. Prominent IR bands were found at 2938, 1640, 1596, 1468, 1362, 1189, 1098, 965, 913, 845, 814, 668, 655, 573, 556, and 530 cm$^{-1}$.

Step 2: Reduction

Into an oven-dried two-liter three-neck round-bottomed flask equipped with a 500 mL pressure-equalizing addition funnel, magnetic stir bar, thermometer, and a nitrogen inlet was added 140.8 g of the crude tosylate of Step 1 and 120 mL of THF. Into the pressure-equalizing addition funnel was placed 600 mL of 1.0 M lithium triethylborohydride in tetrahydrofuran (SUPER-HYDRIDE, purchased from Aldrich). The tetrahydrofuran solution was added to the over one hour. The temperature of the reaction mixture rose to 35–40° C. during the addition. The reaction mixture was refluxed for three hours and then cooled to 25–30° C. using an ice bath. Ten milliliters of de-ionized water was added to the flask to destroy unreacted lithium triethylborohydride. The organoborane was oxidized by adding 300 mL of 3N NaOH followed by the dropwise addition of 30% hydrogen peroxide. This addition was exothermic. The mixture was poured into a 3 L separatory funnel and extracted with three 200 mL portions of hexane. The combined hexane extracts were washed sequentially with two 100 mL portions of de-ionized water and 150 mL of brine. The hexane solution was then dried using anhydrous magnesium sulfate. The hexane was removed from the product by distillation at atmospheric pressure to afford a light yellow oil. The crude product was distilled under reduced pressure. The main fraction distilled at 33–41° C. at 30–34 Pa. The product was analyzed by IR, proton NMR and carbon NMR, and found to be consistent with the desired product.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A medical device comprising a polymer comprising a urethane group, a urea group, or combinations thereof, wherein the polymer comprises a soft segment that is prepared from an isocyanate-containing compound and a compound of the formula:

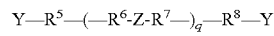

wherein:
 each Y is independently OH or NH$_2$;
 q=1–2000;
 Z is —C(R$^9$)$_2$—;
 R$^5$, R$^6$, R$^7$, and R$^8$ are each independently a straight chain alkylene group having 1–20 carbon atoms; and
 each R$^9$ is independently a straight chain alkyl group having 1–20 carbon atoms;
 and wherein the polymer is substantially free of ether, ester, and carbonate linkages.

2. The medical device of claim 1 wherein q=1–100.

3. The medical device of claim 2 wherein q=2–12.

4. The medical device of claim 1 wherein each Y is OH.

5. The medical device of claim 4 wherein R$^9$ is methyl.

6. A polymer comprising a urethane group, a urea group, or combinations thereof, a soft segment and a group of the formula:

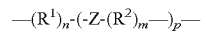

wherein:
 n=0 or 1;
 m=0 or 1;
 p=1–2000;
 R$^1$ and R$^2$ are each independently a saturated or unsaturated aliphatic group, an aromatic group, or combinations thereof, optionally including heteroatoms, with the proviso that R$^2$ includes at least two carbon atoms; and
 Z is —C(R$^3$)$_2$— wherein each R$^3$ is independently a saturated or unsaturated aliphatic group, an aromatic group, or combinations thereof, optionally including heteroatoms, wherein the two R$^3$ groups within —C(R$^3$)$_2$— can be optionally joined to form a ring;
 and wherein the polymer is substantially free of ether, ester, and carbonate linkages.

7. The polymer of claim 6 wherein p=1–100.

8. The polymer of claim 6 wherein p=2–12.

9. The polymer of claim 6 wherein the polymer is a biomaterial.

10. The polymer of claim 6 wherein the polymer is linear, branched, or crosslinked.

11. A polymer comprising a urethane group, a urea group, or combinations thereof, wherein the polymer comprises a soft segment that is prepared from a compound of the formula:

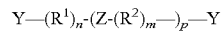

wherein:
 each Y is independently OH or NR$^4$H;
 n=0 or 1;
 m=0 or 1;
 p=1–2000;
 R$^1$ and R$^2$ are each independently a saturated or unsaturated aliphatic group, an aromatic group, or combinations thereof, optionally including heteroatoms;
 Z is —C(R$^3$)$_2$— wherein each R$^3$ is independently a saturated or unsaturated aliphatic group, an aromatic group, or combinations thereof, optionally including heteroatoms, wherein the two $R^3$ groups within
—$C(R^3)_2$— can be optionally joined to form a ring; and each $R^4$ is independently H or a saturated or unsaturated aliphatic group, an aromatic group, or combinations thereof;

with the proviso that at least one of the repeat units -$Z$-$(R^2)_m$— is not a —$C(CH_3)_2CH_2$— group when both Y groups are OH;

and wherein the polymer is substantially free of ether, ester, and carbonate linkages.

12. The polymer of claim 11 wherein p=1–100.

13. The polymer of claim 12 wherein p=2–12.

14. The polymer of claim 11 wherein the polymer is a biomaterial.

15. The polymer of claim 11 wherein the polymer is linear, branched, or crosslinked.

16. A polymer comprising a urethane group, a urea group, or combinations thereof, wherein the polymer comprises a soft segment and that is prepared from an isocyanate-containing compound and a compound of the formula:

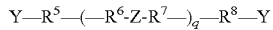

wherein:
each Y is independently OH or $NH_2$;
q=1–2000;
Z is —$C(R^9)_2$—;
$R^5$, $R^6$, $R^7$, and $R^8$ are each independently a straight chain alkylene group having 1–20 carbon atoms; and
each $R^9$ is independently a straight chain alkyl group having 1–20 carbon atoms;

and wherein the polymer is substantially free of ether, ester, and carbonate linkages.

17. The polymer of claim 16 wherein q=1–100.

18. The polymer of claim 17 wherein q=2–12.

19. The polymer of claim 16 wherein each Y is OH.

20. The polymer of claim 19 wherein each $R^9$ methyl.

21. A method of making a polymer comprising a urethane group, a urea group, or combinations thereof, a soft segment comprising a group of the formula —$(R^1)_n$-$(-Z$-$(R^2)_m$—$)_p$—, the method comprising combining an isocyanate-containing compound and a compound of the formula:

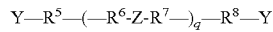

wherein:
each Y is independently OH or $NR^4H$;
n=0 or 1;
m=0 or 1;
p=1–2000;
$R^1$ and $R^2$ are each independently a saturated or unsaturated aliphatic group, an aromatic group, or combinations thereof, optionally including heteroatoms;
Z is —$C(R^3)_2$— wherein each $R^3$ is independently a saturated aliphatic group, an aromatic group, or combinations thereof, optionally including heteroatoms, wherein the two $R^3$ groups within —$C(R^3)_2$— can be optionally joined to form a ring; and
each $R^4$ is independently H or a saturated or unsaturated aliphatic group, an aromatic group, or combinations thereof;

with the proviso that at least one of the repeat units -$Z$-$(R^2)_m$— is not a —$C(CH_3)_2CH_2$— group when both Y groups are OH;

and wherein the polymer is substantially free of ether, ester, and carbonate linkages.

22. A method of making a polymer comprising a urethane group, a urea group, or combinations thereof, a soft segment and a group of the formula —$C(R^9)_2$—, the method comprising combining an isocyanate-containing compound and a compound of the formula:

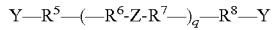

wherein:
each Y is independently OH or $NH_2$;
q=1–2000;
Z is —$C(R^9)_2$—;
$R^5$, $R^6$, $R^7$, and $R^8$ are each independently a straight chain alkylene group having 1–20 carbon atoms; and
each $R^9$ is independently a straight chain alkyl group having 1–20 carbon atoms;

and wherein the polymer is substantially free of ether, ester, and carbonate linkages.

23. The method of claim 22 wherein q=1–100.

24. The method of claim 22 wherein q=2–12.

25. The method of claim 22 wherein each Y is OH.

26. The method of claim 25 wherein each $R^9$ is methyl.

27. A medical device comprising a polymer comprising a urethane group, a urea group, or combinations thereof, wherein the polymer is prepared from an isocyanate-containing compound and a compound of the formula:

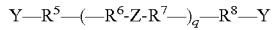

wherein:
each Y is independently OH or $NH_2$;
q=2–20;
Z is —$C(R^9)_2$—;
$R^5$, $R^6$, $R^7$, and $R^8$ are each independently a straight chain alkylene group having 1–20 carbon atoms; and
each $R^9$ is independently a straight chain alkyl group having 1–20 carbon atoms.

28. A polymer comprising a urethane group, a urea group, or combinations thereof, and a group of the formula:

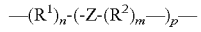

wherein:
n=0 or 1;
m=0 or 1;
p=2–20;
$R^1$ and $R^2$ are each independently a saturated or unsaturated aliphatic group, an aromatic group, or combinations thereof, optionally including heteroatoms, with the proviso that $R^2$ includes at least two carbon atoms; and
Z is —$C(R^3)_2$— wherein each $R^3$ is independently a saturated or unsaturated aliphatic group, an aromatic group, or combinations thereof, optionally including heteroatoms, wherein the two $R^3$ groups within —$C(R^3)_2$— can be optionally joined to form a ring.

29. A polymer comprising a urethane group, a urea group, or combinations thereof, wherein the polymer is prepared from a compound of the formula:

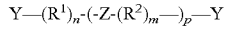

wherein:
each Y is independently OH or $NR^4H$;
n=0 or 1;

m=0 or 1;

p=2–20;

$R^1$ and $R^2$ are each independently a saturated or unsaturated aliphatic group, an aromatic group, or combinations thereof, optionally including heteroatoms;

Z is $—C(R^3)_2—$ wherein each $R^3$ is independently a saturated or unsaturated aliphatic group, an aromatic group, or combinations thereof, optionally including heteroatoms, wherein the two $R^3$ groups within $—C(R^3)_2—$ can be optionally joined to form a ring; and each $R^4$ is independently H or a saturated or unsaturated aliphatic group, an aromatic group, or combinations thereof;

with the proviso that at least one of the repeat units $-Z-(R^2)_m—$ is not a $—C(CH_3)_2CH_2—$ group when both Y groups are OH.

30. A polymer comprising a urethane group, a urea group, or combinations thereof, wherein the polymer is prepared from an isocyanate-containing compound and a compound of the formula:

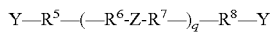

wherein:

each Y is independently OH or $NH_2$;

q=2–20;

Z is $—C(R^9)_2—$;

$R^5$, $R^6$, $R^7$, and $R^8$ are each independently a straight chain alkylene group having 1–20 carbon atoms; and each $R^9$ is independently a straight chain alkyl group having 1–20 carbon atoms.

31. A method of making a polymer comprising a urethane group, a urea group, or combinations thereof, and a group of the formula $—(R^1)_n-(-Z-(R^2)_m—)_p—$, the method comprising combining an isocyanate-containing compound and a compound of the formula:

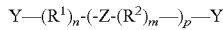

wherein:

each Y is independently OH or $NR^4H$;

n=0 or 1;

m=0 or 1;

p=2–20;

$R^1$ and $R^2$ are each independently a saturated or unsaturated aliphatic group, an aromatic group, or combinations thereof, optionally including heteroatoms;

Z is $—C(R^3)_2—$ wherein each $R^3$ is independently a saturated aliphatic group, an aromatic group, or combinations thereof, optionally including heteroatoms, wherein the two $R^3$ groups within $—C(R^3)_2—$ can be optionally joined to form a ring; and each $R^4$ is independently H or a saturated or unsaturated aliphatic group, an aromatic group, or combinations thereof;

with the proviso that at least one of the repeat units $-Z-(R^2)_m—$ is not a $—C(CH_3)_2CH_2—$ group when both Y groups are OH.

32. A method of making a polymer comprising a urethane group, a urea group, or combinations thereof, and a group of the formula $—C(R^9)_2—$, the method comprising combining an isocyanate-containing compound and a compound of the formula:

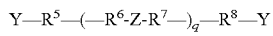

wherein:

each Y is independently OH or $NH_2$;

q=2–20;

Z is $—C(R^9)_2—$;

$R^5$, $R^6$, $R^7$, and $R^8$ are each independently a straight chain alkylene group having 1–20 carbon atoms; and each $R^9$ is independently a straight chain alkyl group having 1–20 carbon atoms.

33. The medical device of claim 27 wherein each Y is OH.

34. The medical device of claim 33 wherein each $R^9$ is methyl.

35. The medical device of claim 27 wherein q=2–12.

36. The polymer of claim 28 wherein the polymer is a biomaterial.

37. The polymer of claim 28 wherein the polymer is linear, branched, or crosslinked.

38. The polymer of claim 28 wherein p=2–12.

39. The polymer of claim 29 wherein the polymer is a biomaterial.

40. The polymer claim 29 wherein the polymer is linear, branched, or crosslinked.

41. The polymer of claim 29 wherein p=2–12.

42. The polymer of claim 30 wherein each Y is OH.

43. The polymer of claim 42 wherein each $R^9$ is methyl.

44. The polymer of claim 30 wherein q=2–12.

45. The method of claim 31 wherein the polymer comprises a segmented polyurethane.

46. The method of claim 31 wherein the polymer is substantially free of ether, ester, and carbonate linkages.

47. The method of claim 31 wherein the polymer is a biomaterial.

48. The method of claim 31 wherein the polymer is linear, branched, or crosslinked.

49. The method of claim 31 wherein p=2–12.

50. The method of claim 32 wherein each Y is OH.

51. The method of claim 50 wherein each $R^9$ is methyl.

52. The method of claim 32 wherein q=2–12.

53. The method of claim 21 wherein the polymer comprises a segmented polyurethane.

54. The method of claim 21 wherein the polymer is a biomaterial.

55. The method of claim 21 wherein the polymer is linear, branched, or crosslinked.

56. The method of claim 21 wherein p=1–100.

57. The method of claim 56 wherein p=2–12.

58. The polymer of claim 28 wherein the polymer comprises a segmented polyurethane.

59. The polymer of claim 28 wherein the polymer is substantially free of ether, ester, and carbonate linkages.

60. The polymer of claim 29 wherein the polymer comprises a segmented polyurethane.

61. The polymer of claim 29 wherein the polymer is substantially free of ether, ester, and carbonate linkages.

* * * * *